US009931141B2

(12) United States Patent
Jimenez

(10) Patent No.: US 9,931,141 B2
(45) Date of Patent: Apr. 3, 2018

(54) METHOD AND APPARATUS FOR JOINT FUSION

(71) Applicant: Ex Technology, LLC, Gering, NE (US)

(72) Inventor: Omar F. Jimenez, Gering, NE (US)

(73) Assignee: Ex Technology, LLC, Gering, NE (US)

( * ) Notice: Subject to any disclaimer, the term of this patent is extended or adjusted under 35 U.S.C. 154(b) by 0 days.

(21) Appl. No.: 14/554,472

(22) Filed: Nov. 26, 2014

(65) Prior Publication Data

US 2016/0143671 A1 May 26, 2016

(51) Int. Cl.
| A61B 17/86 | (2006.01) |
| A61B 17/70 | (2006.01) |
| A61B 17/16 | (2006.01) |
| A61B 17/56 | (2006.01) |

(52) U.S. Cl.
CPC ...... *A61B 17/7055* (2013.01); *A61B 17/1671* (2013.01); *A61B 17/7082* (2013.01); *A61B 17/863* (2013.01); *A61B 17/864* (2013.01); *A61B 2017/564* (2013.01)

(58) Field of Classification Search
CPC ... A61B 17/86; A61B 17/8625; A61B 17/863; A61B 17/8635; A61B 17/864; A61B 17/8645; A61B 17/8685
See application file for complete search history.

(56) References Cited

U.S. PATENT DOCUMENTS

| 4,175,555 | A | * | 11/1979 | Herbert ............... | A61B 17/863 411/415 |
| 5,139,499 | A | * | 8/1992 | Small .................. | A61B 17/864 606/104 |
| 5,259,398 | A | * | 11/1993 | Vrespa ............................ | 128/898 |
| 5,470,334 | A | * | 11/1995 | Ross et al. ..................... | 606/916 |
| 5,743,912 | A | * | 4/1998 | Lahille et al. .................. | 606/65 |
| 5,827,285 | A | * | 10/1998 | Bramlet ......................... | 606/60 |
| 7,559,951 | B2 | | 7/2009 | DiSilvestro et al. | |

(Continued)

FOREIGN PATENT DOCUMENTS

| EP | 1525863 A2 | 4/2005 |
| WO | WO 2012/174485 A1 | 12/2012 |
| WO | WO 2013/131493 A1 | 9/2013 |

OTHER PUBLICATIONS

Brochure: "Capture Facet Fixation System," Spineology, Inc., Mar. 2012, 4 pages.

(Continued)

*Primary Examiner* — Nicholas Woodall
(74) *Attorney, Agent, or Firm* — Patterson Thuente Pedersen, P.A.

(57) ABSTRACT

A system for implanting an implant screw into one or more bones of a patient, such as the sacrum and the ilium, can include a rod and a screw. The screw can be generally hollow and have a blunt distal end. The rod can include a threaded and pointed distal end that is inserted through the rod to drive the screw through the bones. Once the screw is at a desired position, the rod can be removed such that the sharp driving edge used to seat the screw does not remain in the bone. The system can further include an extraction tool having a generally hollow body sized to be inserted over the rod and a distally located screw engagement portion configured to engage the screw to adjust positioning of the screw after it is initially seated.

8 Claims, 25 Drawing Sheets

(56) References Cited

U.S. PATENT DOCUMENTS

| | | | |
|---|---|---|---|
| 7,736,381 B2 * | 6/2010 | Biedermann et al. | 606/301 |
| 7,854,765 B2 | 12/2010 | Moskowitz et al. | |
| 7,938,848 B2 | 5/2011 | Sweeney | |
| 8,257,356 B2 | 9/2012 | Bleich et al. | |
| 8,308,783 B2 * | 11/2012 | Morris et al. | 606/328 |
| 8,348,949 B2 | 1/2013 | Butler et al. | |
| 8,394,109 B2 | 3/2013 | Hutton et al. | |
| 8,414,648 B2 | 4/2013 | Reiley | |
| 8,442,621 B2 | 5/2013 | Gorek et al. | |
| 8,551,171 B2 | 10/2013 | Johnson et al. | |
| 8,579,912 B2 | 11/2013 | Isaza et al. | |
| 8,679,168 B2 * | 3/2014 | McNamara et al. | 606/308 |
| 8,734,447 B1 | 5/2014 | Michaelson | |
| 8,734,456 B2 | 5/2014 | Stark | |
| 8,734,462 B2 | 5/2014 | Reiley et al. | |
| 8,740,912 B2 | 6/2014 | Stark | |
| 8,840,651 B2 | 9/2014 | Reiley | |
| 9,452,007 B1 * | 9/2016 | McGuire | A61B 17/8615 |
| 2002/0169453 A1 | 11/2002 | Berger et al. | |
| 2005/0149031 A1 * | 7/2005 | Ciccone | A61B 17/1615 606/280 |
| 2005/0222575 A1 | 10/2005 | Ciccone et al. | |
| 2005/0261695 A1 * | 11/2005 | Cragg | A61B 17/1671 606/86 R |
| 2008/0234682 A1 * | 9/2008 | Park | A61B 17/0401 606/75 |
| 2008/0275458 A1 | 11/2008 | Bleich et al. | |
| 2010/0010496 A1 | 1/2010 | Isaza et al. | |
| 2010/0036384 A1 | 2/2010 | Gorek et al. | |
| 2010/0036443 A1 | 2/2010 | Hutton et al. | |
| 2010/0217329 A1 * | 8/2010 | Brown | A61B 17/742 606/301 |
| 2011/0060373 A1 * | 3/2011 | Russell et al. | 606/304 |
| 2012/0095560 A1 | 4/2012 | Donner | |
| 2012/0179163 A1 | 7/2012 | Housman et al. | |
| 2012/0191191 A1 | 7/2012 | Trieu | |
| 2012/0197311 A1 | 8/2012 | Kirschman | |
| 2012/0296428 A1 | 11/2012 | Donner | |
| 2013/0238093 A1 | 9/2013 | Mauldin et al. | |
| 2013/0282012 A1 | 10/2013 | Stark | |
| 2014/0012340 A1 | 1/2014 | Beck et al. | |
| 2014/0031934 A1 | 1/2014 | Trieu | |
| 2014/0031935 A1 | 1/2014 | Donner et al. | |
| 2014/0046380 A1 | 2/2014 | Asfora | |
| 2014/0046381 A1 | 2/2014 | Asfora | |
| 2014/0046382 A1 | 2/2014 | Asfora | |
| 2014/0046383 A1 | 2/2014 | Asfora | |
| 2014/0067063 A1 | 3/2014 | Bonutti | |
| 2014/0088707 A1 | 3/2014 | Donner et al. | |
| 2014/0121707 A1 | 5/2014 | Stark | |
| 2014/0200618 A1 | 7/2014 | Donner et al. | |

OTHER PUBLICATIONS

Endres et al., "Outcome of Distraction Interference Arthrodesis of the Sacroiliac Joint for Sacroiliac Arthritis," IJO—Indian Journal of Orthopaedics, 2013, vol. 47, Issue 5, 3 pages.

Sonntag et al., "ATLANTIS Anterior Cervical Plate System Surgical Technique," Medtronic Sofamor Danek, 2002, 39 pages.

Technical Brochure: "Capture Facet Fixation System," Spineology, Inc., Apr. 2010, 11 pages.

Technique Guide: Cannulated Pangea System, "A Comprehensive Cannulated Pedicle Screw Fixation System for Posterior Stabilization of Spinal Segments," Synthes Spine, 2007, 47 pages.

Website print out: Anatomy Conserving Surgery, "Capture Facet Fixation System," Spineology, Inc., 2009-2015, 1 page.

Website print out: Minimally Invasive Spine Surgery, "Percutaneous Lumbar Pedicle Screws," The Spine Center, 2015, 2 pages.

Website print out: SAMBA Screw System Available Nationwide, "Minimally Invasive Solution for the Treatment of SI-Joint Dysfunction Launches Nationally," Today's Medical Developments, Apr. 20, 2013, 3 pages.

X-spine Product Guide, "Silex Sacroiliac Joint Fusion System," X-spine Systems, Inc., 2013, 52 pages.

PCT Application No. PCT/US2015/061571, filed Nov. 19, 2015, Search Report and Written Opinion dated Apr. 19, 2016, 20 pages.

* cited by examiner

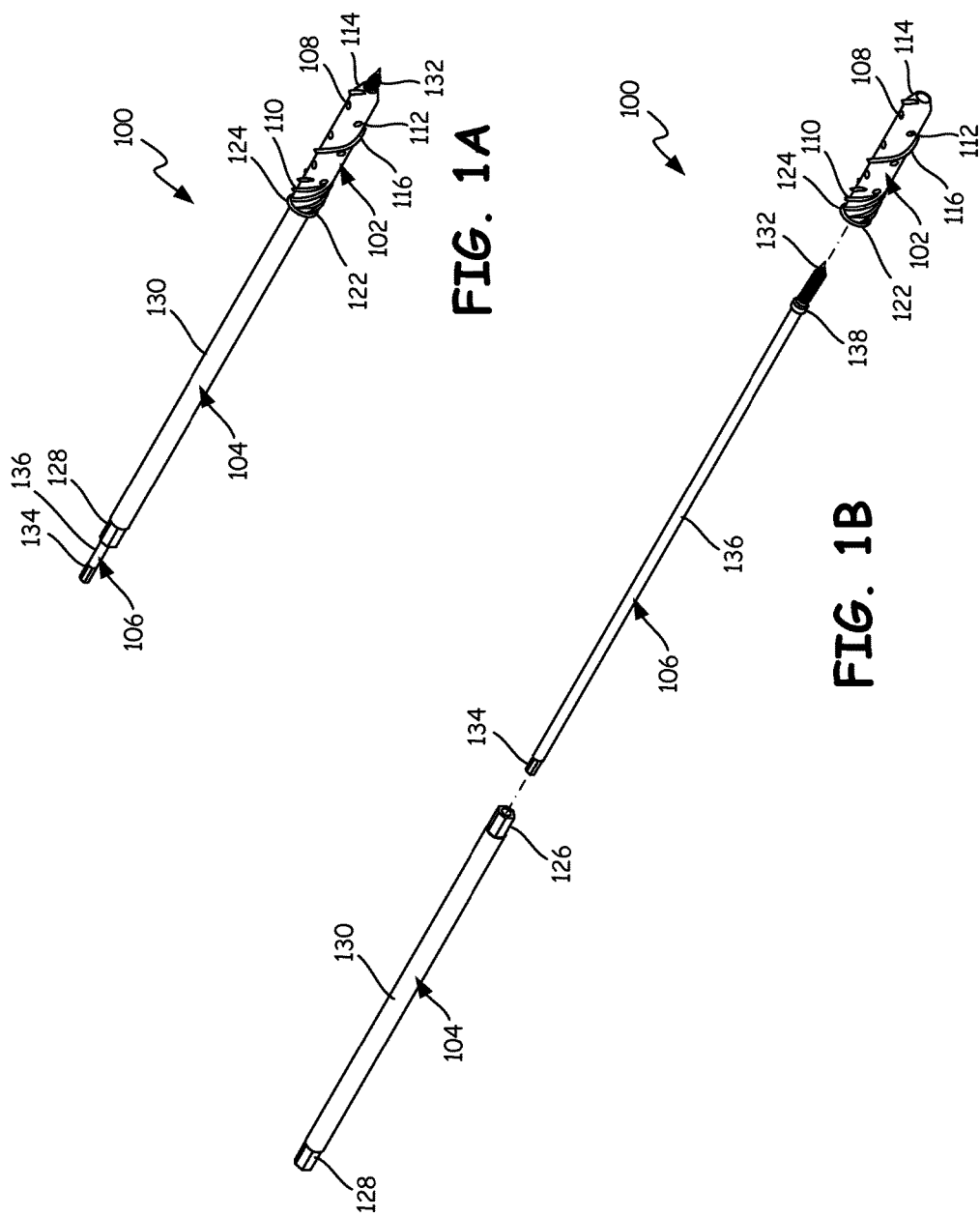

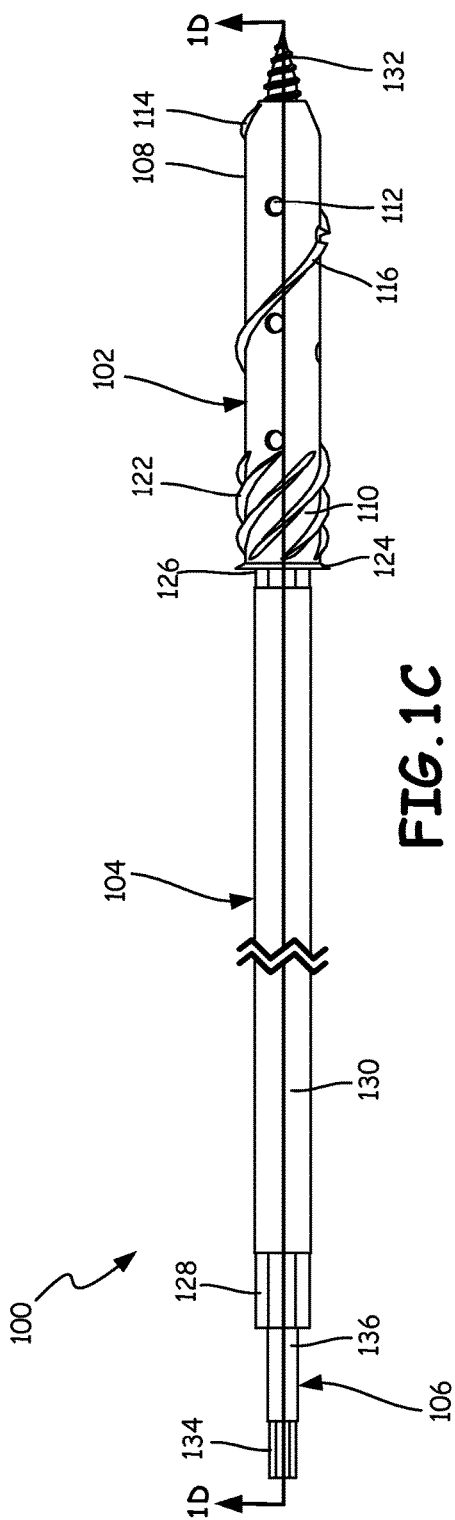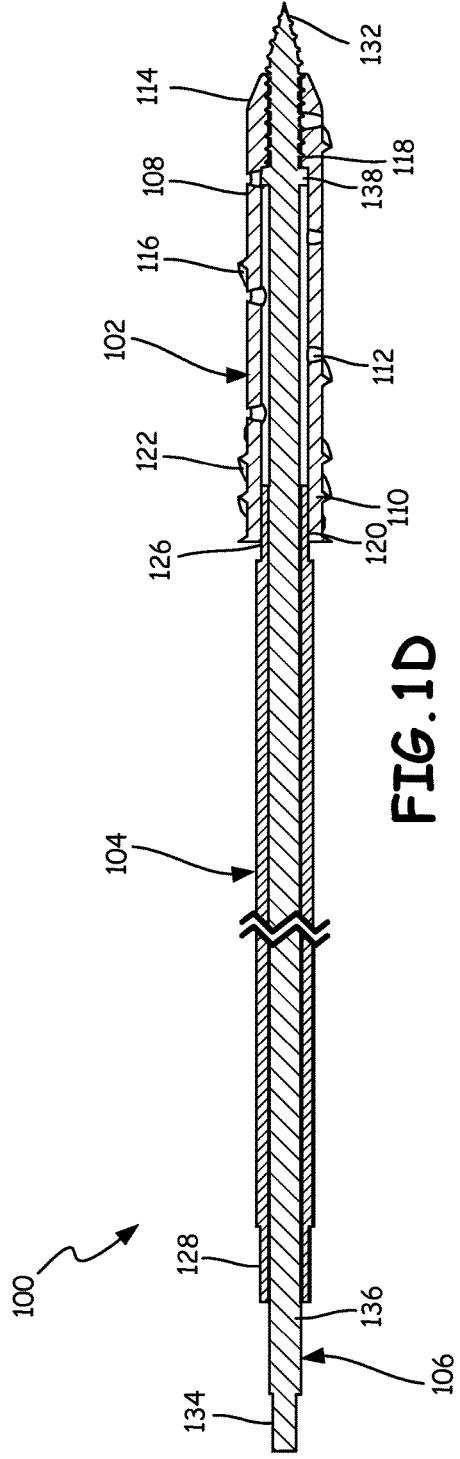

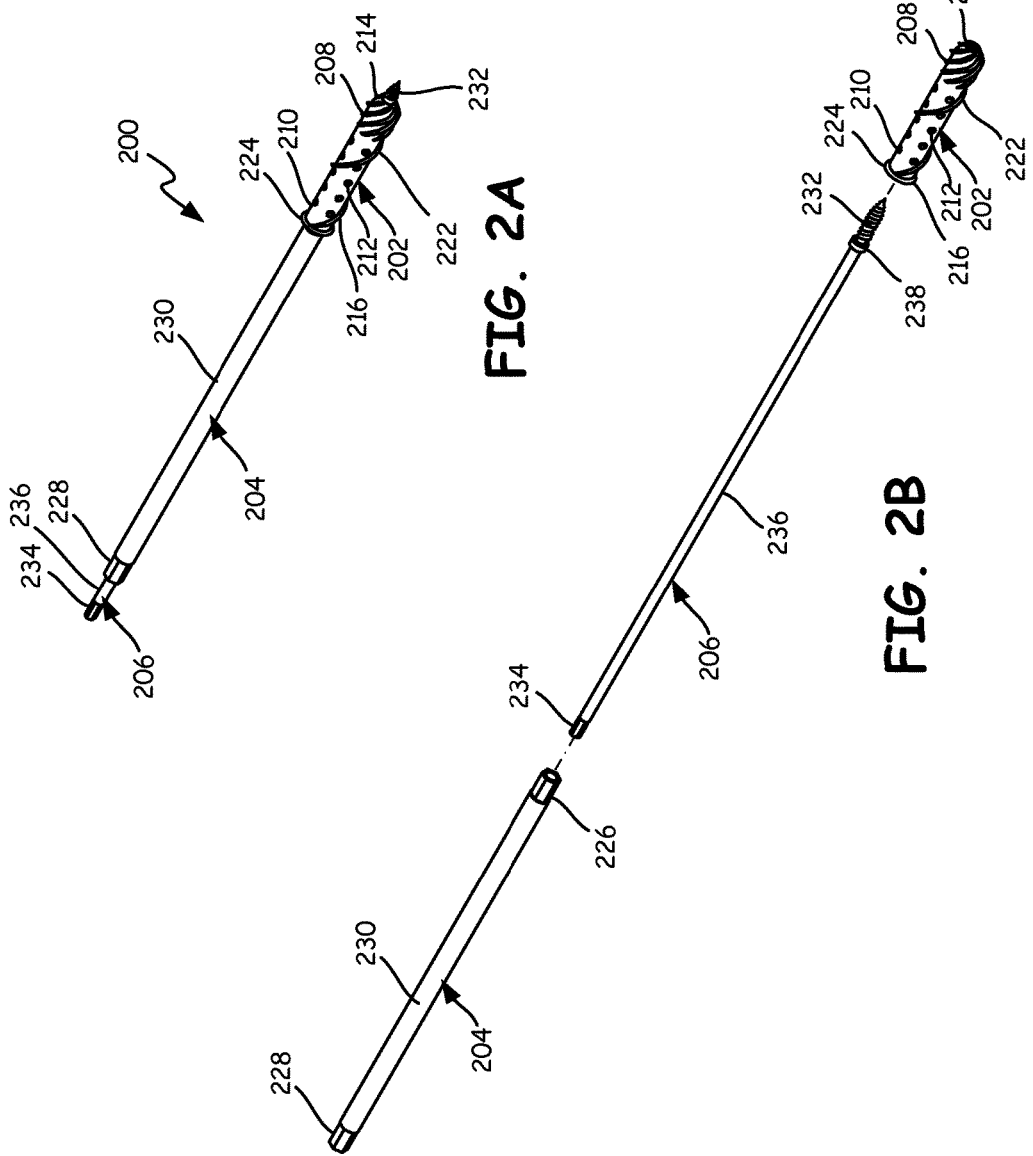

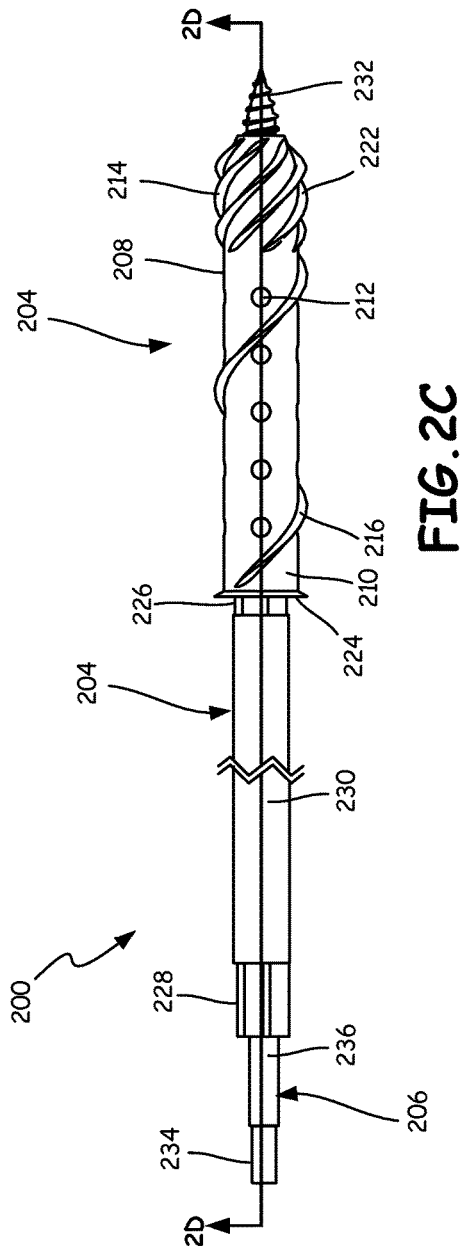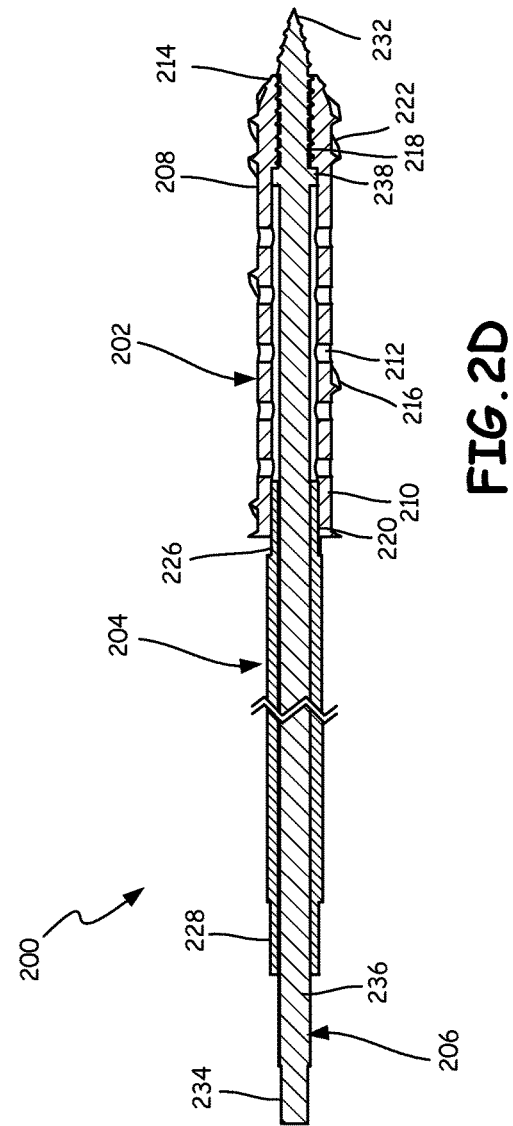

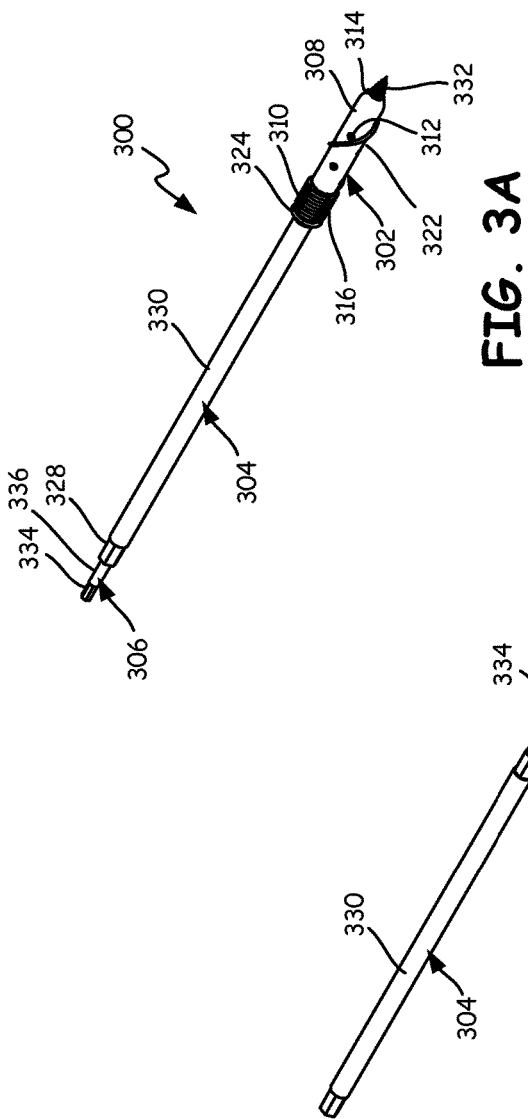
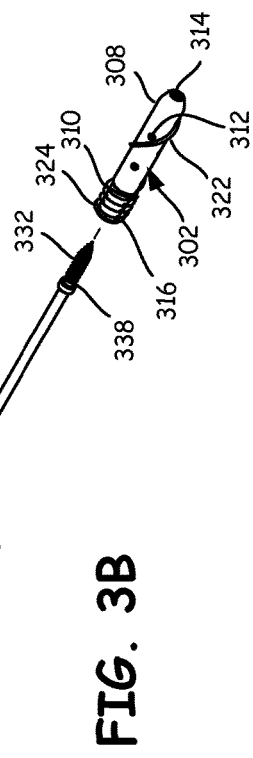
FIG. 3A
FIG. 3B

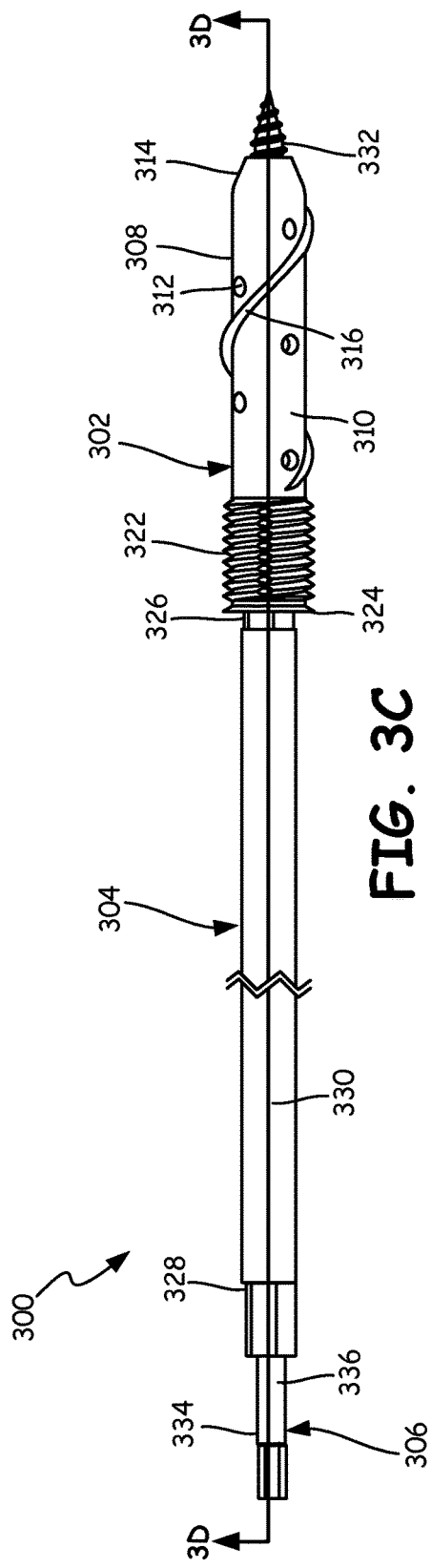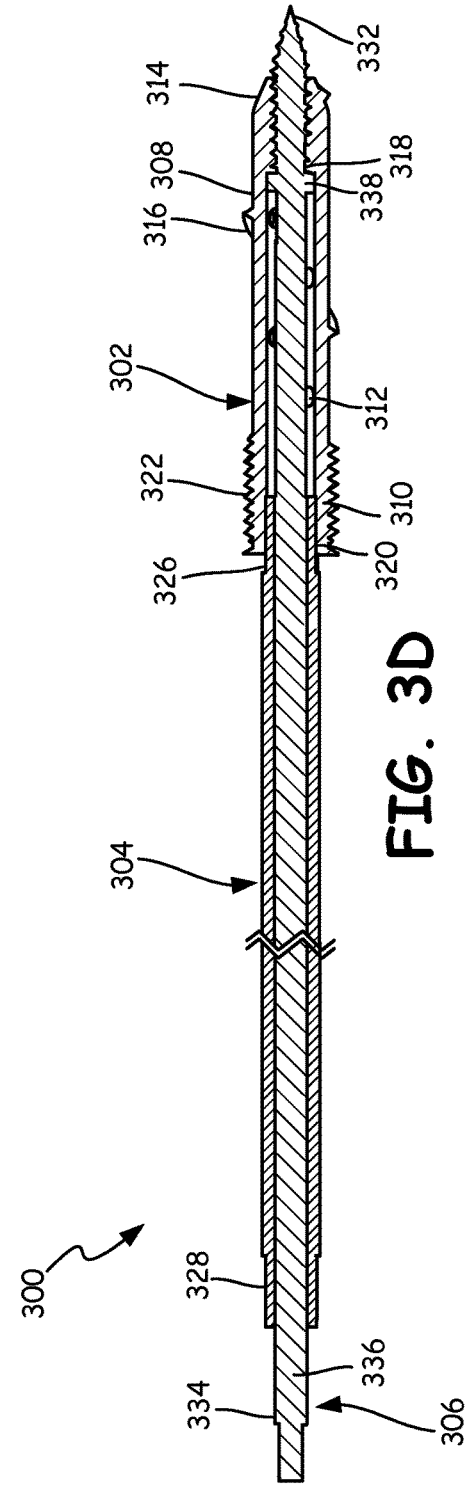

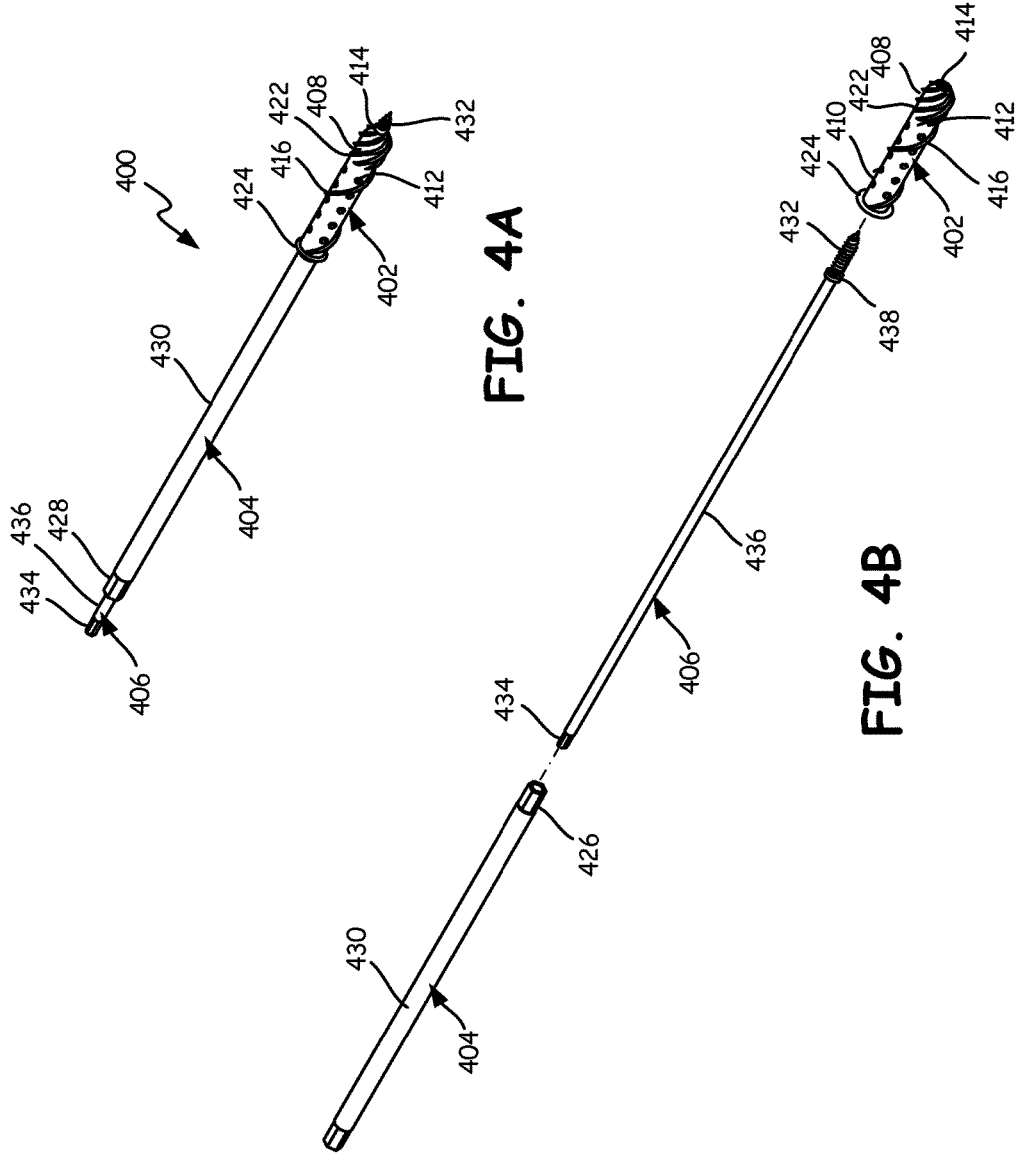

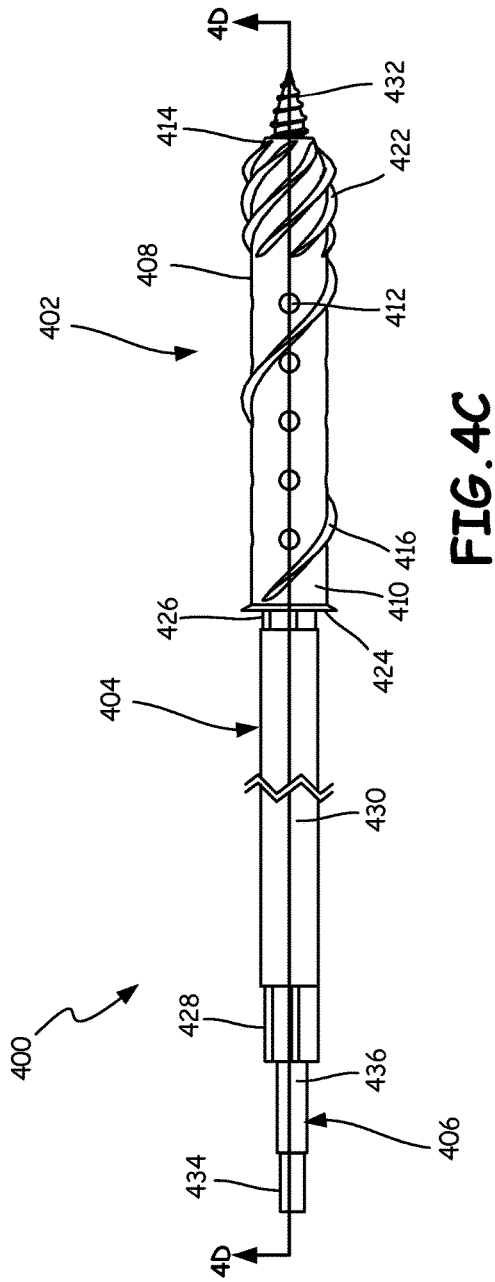
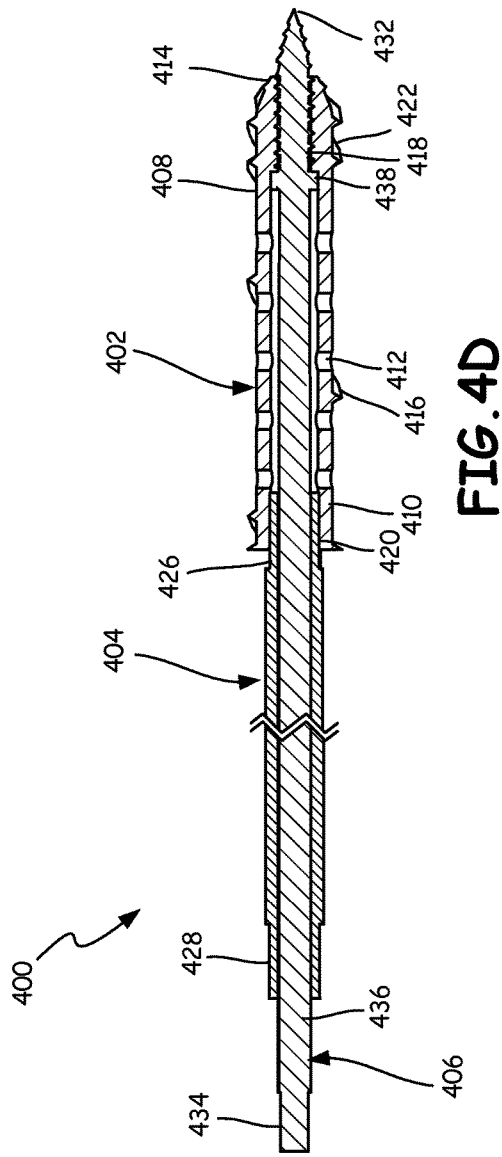

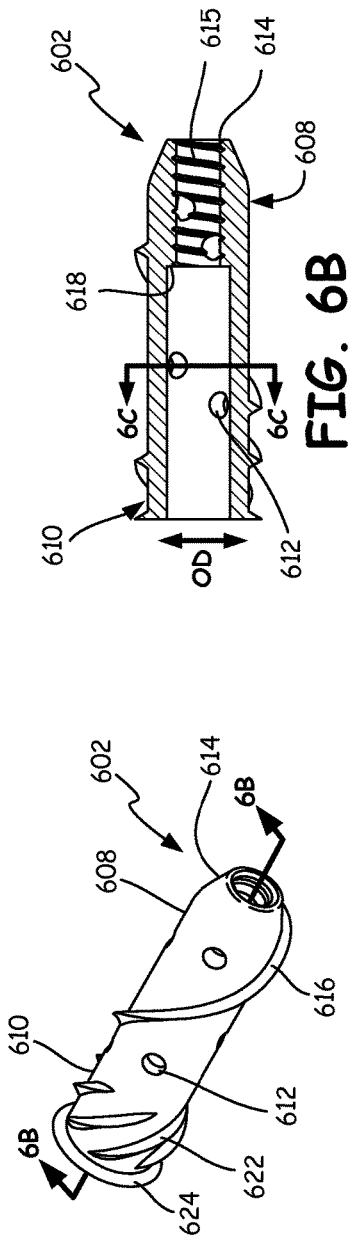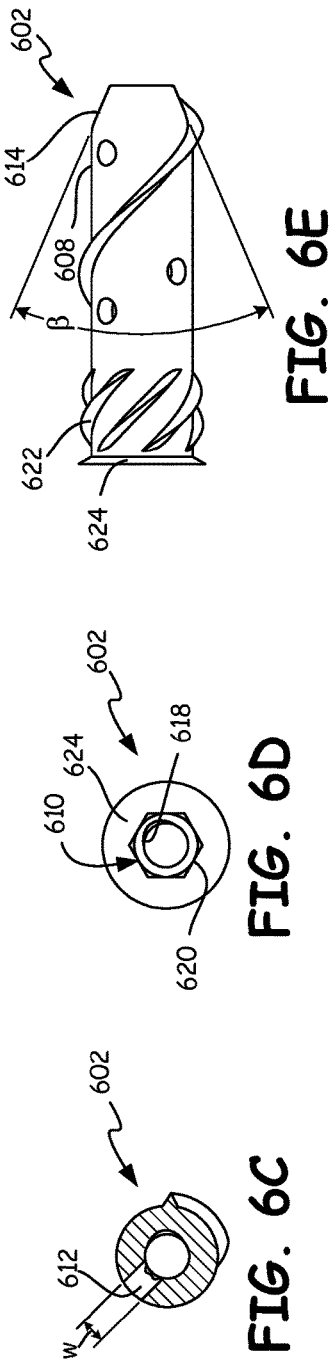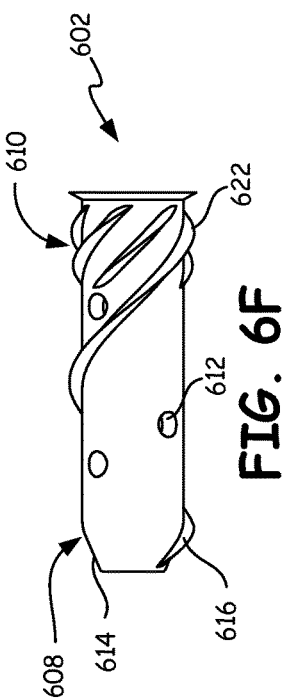

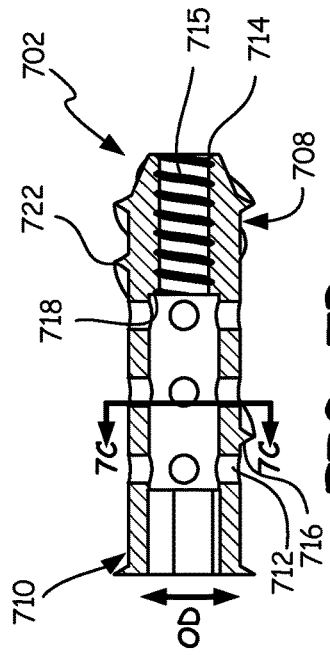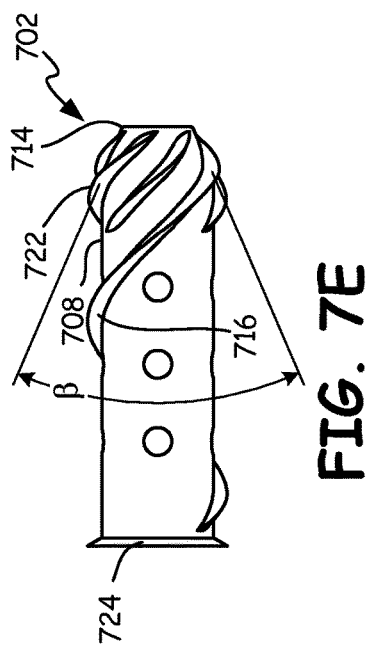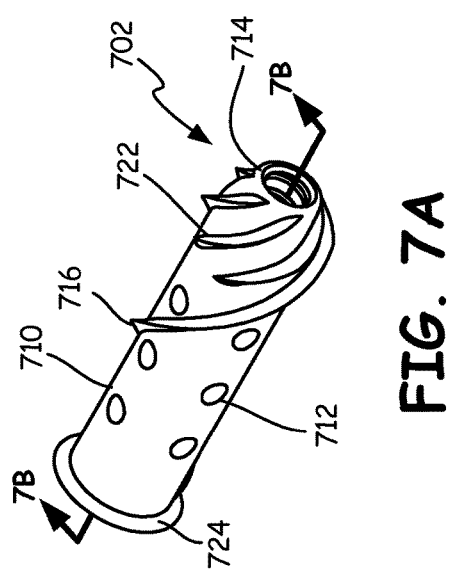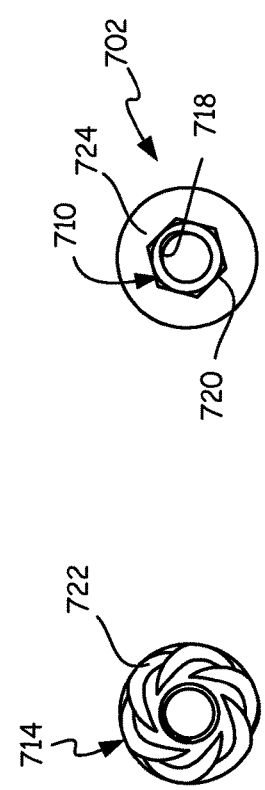
FIG. 7A
FIG. 7B
FIG. 7C
FIG. 7D
FIG. 7E

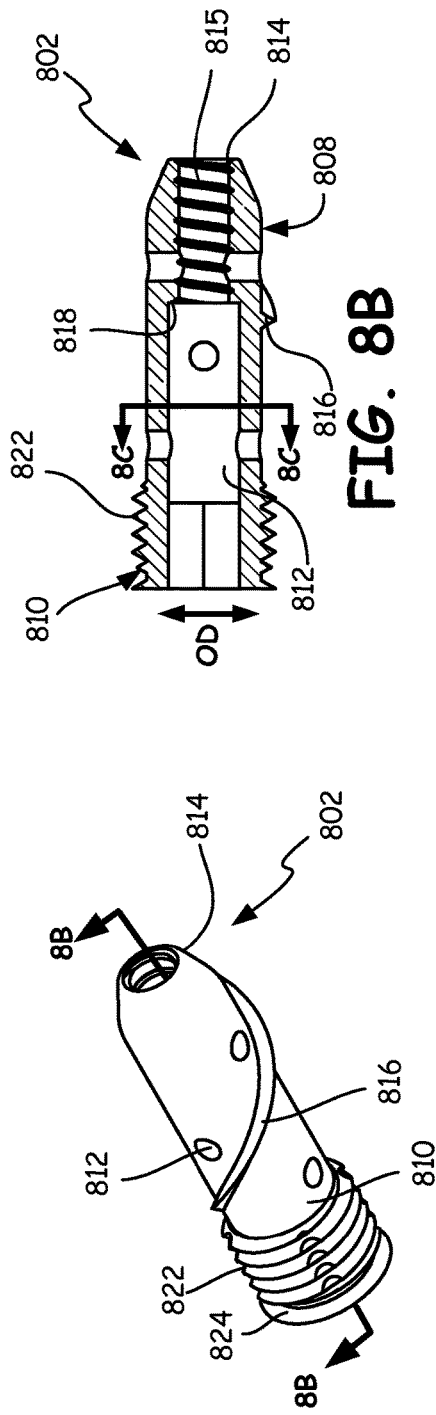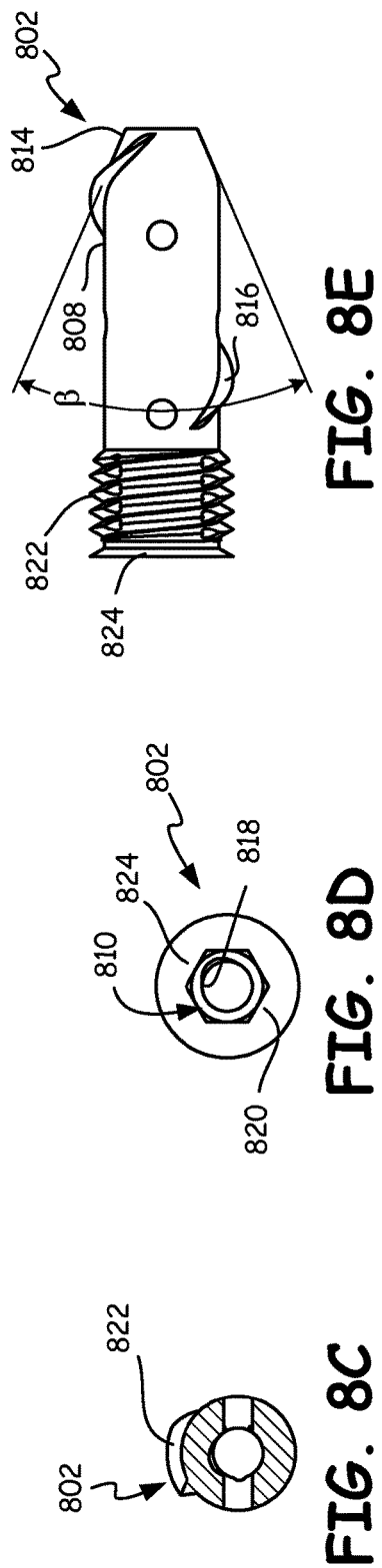

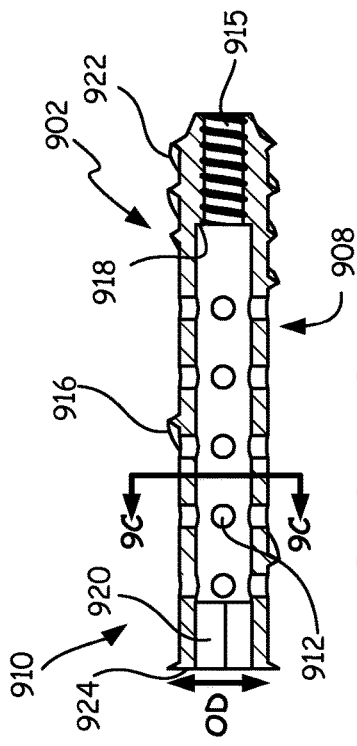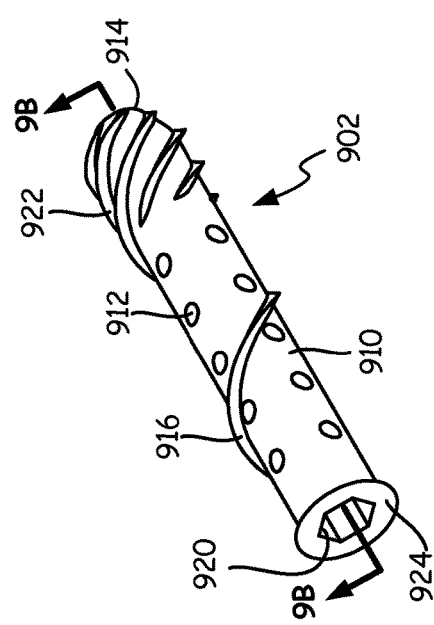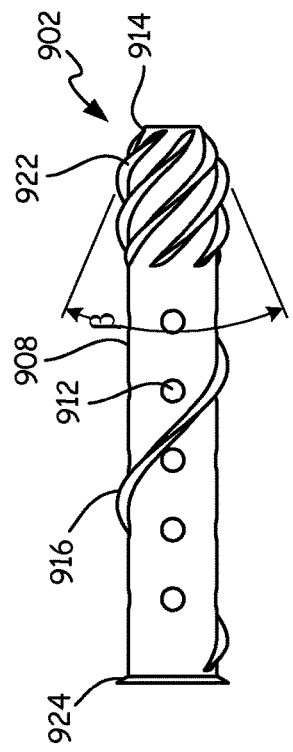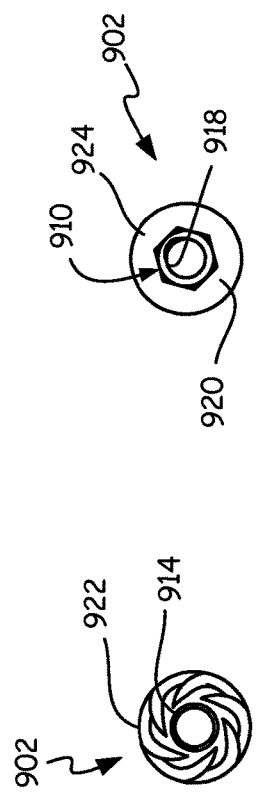

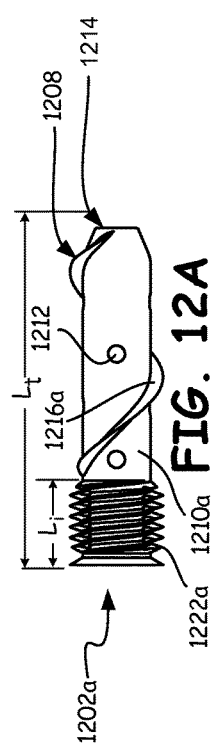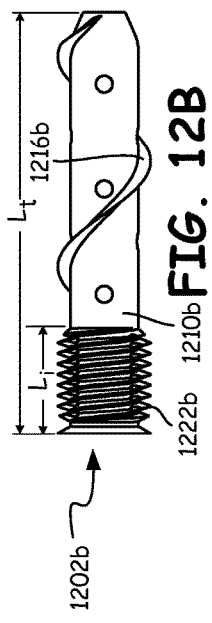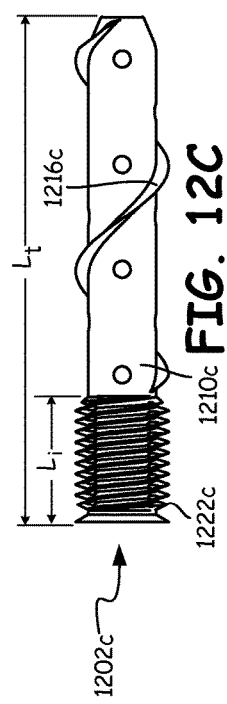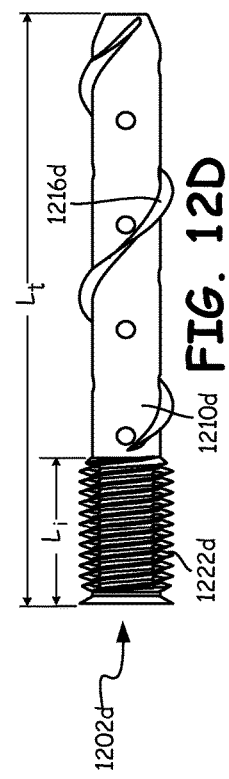

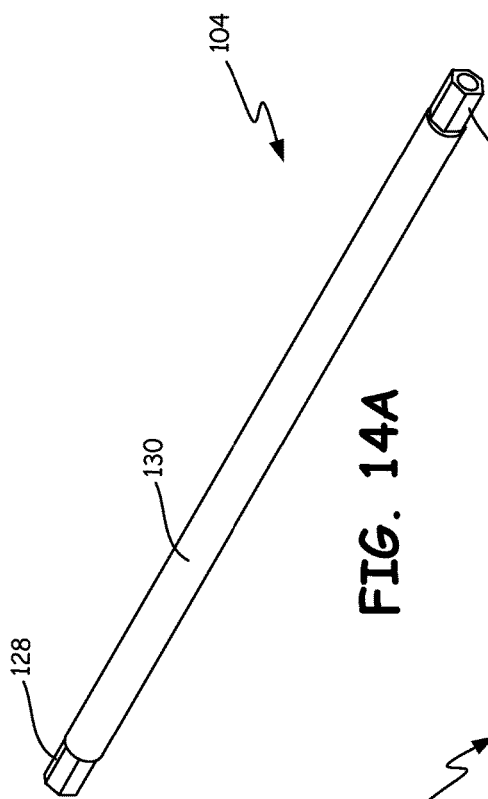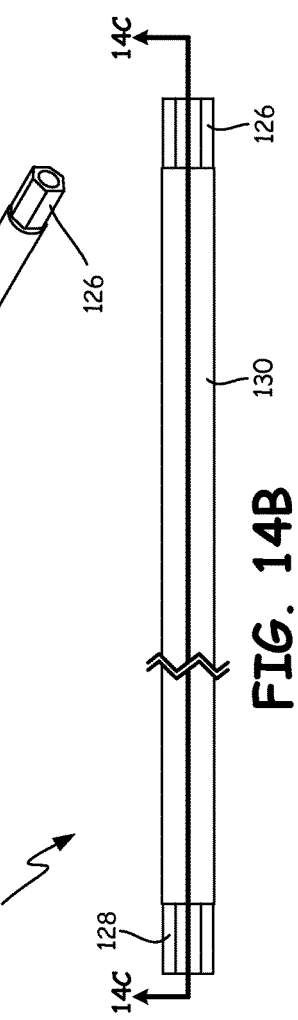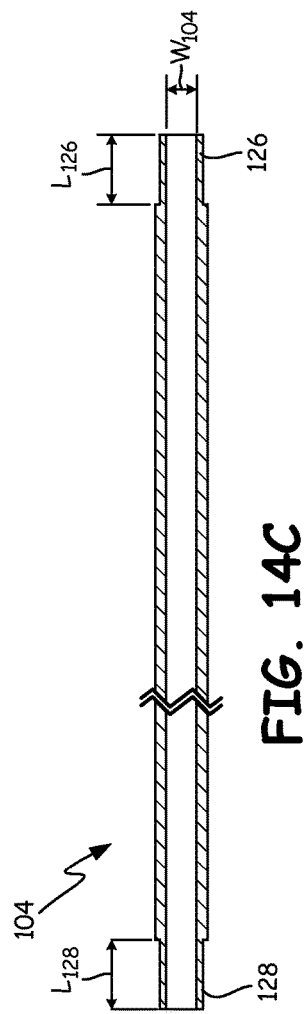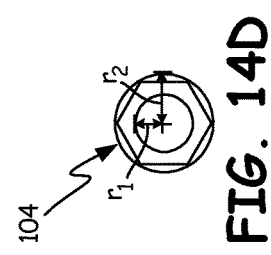

METHOD AND APPARATUS FOR JOINT FUSION

TECHNICAL FIELD

Embodiments relate generally to apparatus and methods for attaching and promoting fusion of two bones, and more particularly to interconnection and fusion of a sacrum and an ilium.

BACKGROUND

One cause of lower back pain is stress across the sacroiliac joint. Sacroiliac joint fusion can relieve stress on the sacroiliac joint by stabilizing the sacrum and ilium to one another via one or more implants, such as screws. These conventional implants pass laterally across the joint and prevent relative movement between the bones.

Conventionally, implanting such devices to fuse the sacrum and ilium has included drilling through the sacrum and ilium, using a tap assembly to create threading, and then inserting a threaded screw through the joint and across both bones. Other implants include inserting titanium wedges across the joint. This technique involves drilling through a threaded pin and then using a shaped broach to create the shape of the implant. The implant is then tamped through the joint. Thereafter, bone fusion can occur around the implants. In some cases, bone grafting material can be packed into or around the implant to promote bone fusion.

In order to insert such implant screws, often a pointed-tip screw is attached to a driving shaft, and is inserted to the appropriate depth to hold the bones in a fixed spatial relationship. Some conventional insert screws also have passages through which bone grafting material can be either packed prior to insertion, or routed during or shortly after the screw is placed in the bone. After the implant is placed, discomfort or injury can be caused by the sharp tip of the screw being near the sacral foramina.

SUMMARY

In some embodiments, an implant screw is adapted for implantation into one or more bones of a patient, such as the sacrum and the ilium. The implant screw can include a proximal portion having an open proximal end, a generally cylindrical outer surface and an inner surface defining a generally hollow interior. The inner surface can further define engagement features adapted to be engaged to enact rotation of the implant screw. The screw can further include a distal portion unitarily formed with the proximal portion, the distal portion having a body portion with a generally cylindrical outer surface and a frustoconical distal end portion defining an open distal tip. The distal portion can further include a threaded inner surface defining a generally hollow interior, the inner surface further defining an inwardly projecting stop ledge such that the generally hollow interior of the distal portion is narrower than the generally hollow interior of the proximal portion.

In some embodiments, a system for implanting an implant screw into one or more bones of a patient, such as the sacrum and the ilium, includes a rod and a screw. The rod can include a generally cylindrical body and a threaded distal portion including a distal screw tip. The implant screw can include a generally cylindrical outer surface including a blunt distal end and an inner surface defining a hollow interior. The hollow interior can include a threaded portion adapted to enable passage of the threaded distal portion of the rod through the hollow interior via rotation of the rod in a first direction such that the distal screw tip of the rod extends distally from the blunt distal end of the implant screw and rotation of the rod in a second direction withdraws the threaded distal portion of the rod from the hollow interior of the screw. In certain embodiments, the system can further include an extraction tool having a generally hollow body sized to be inserted over the rod and a distally located screw engagement portion configured to engage the screw such that rotation of the extraction tool causes rotation of the screw.

BRIEF DESCRIPTION OF THE DRAWINGS

The invention can be more completely understood in consideration of the following detailed description of various embodiments of the invention in connection with the accompanying drawings, in which:

FIG. 1A is a perspective view of a bone screw implant system, according to an embodiment;

FIG. 1B is an exploded view of the bone screw implant system of FIG. 1A;

FIG. 1C is an elevation view of a bone screw implant system, according to an embodiment;

FIG. 1D is an end view of the bone screw implant system of FIG. 1A along line 1D-1D;

FIGS. 2A-2D depict a second embodiment of a bone screw implant system;

FIGS. 3A-3D depict a third embodiment of a bone screw implant system;

FIGS. 4A-4D depict a fourth embodiment of a bone screw implant system;

FIGS. 6A-6F depict an implant screw, according to an embodiment;

FIGS. 7A-7E depict an implant screw according to another embodiment;

FIGS. 8A-8E depict an implant screw according to yet another embodiment;

FIGS. 9A-9E depict an implant screw according to yet another embodiment;

FIGS. 12A-12D are elevation views of implant screws having different lengths, according to a third thread arrangement;

FIGS. 14A-14D illustrate an extraction tool, according to an embodiment;

Figure 5A:
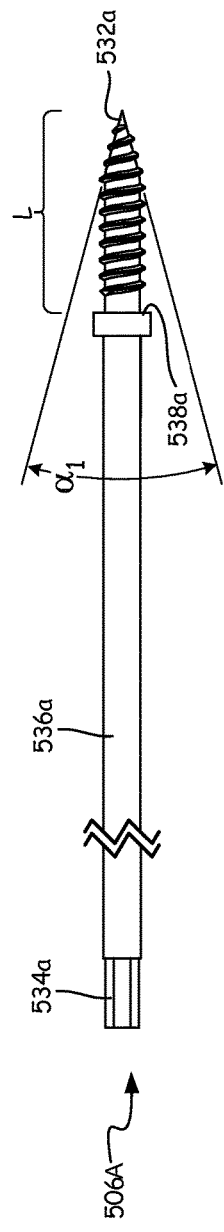
FIGS. 5A-5C are elevation views of three embodiments of a rod configured for use in a bone screw implant system.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

In various embodiments, an insert screw is configured to attach two objects, such as an ilium and a sacrum. The apparatus used to install the insert screw includes a rod having a tip, which is removed once the insert screw is in place. As such, the insert screw fastens the ilium and sacrum to one another without leaving a pointed tip in the bone, and bone growth material can be injected into the insert screw to be delivered to the side or forward with respect to the installation direction.

FIGS. 1A-1D depict a bone screw implant system 100, according to an embodiment of the present invention. System 100 includes implant screw 102, extraction tool 104, and rod 106. Implant screw 102 includes sacral portion 108 and ilial portion 110, and defines apertures 112. Sacral portion 108 includes frustoconical end 114, sacral thread 116, and stop ledge 118. Ilial portion 110 includes engagement portion 120, ilial threads 122, and screw flange 124. Extraction tool 104 includes screw engagement portion 126, driver engagement portion 128, and body portion 130 there between. Rod 106 includes tip 132, rod driver engagement portion 134, shaft 136, and rod flange 138. FIGS. 1A and 1B illustrate the nested manner in which system 100 can be arranged.

In operation, implant screw 102, extraction tool 104, and rod 106 can be nested as shown with respect to FIG. 1A, and will co-rotate with one another due to interlocking engagement between their various portions, as described in more detail with respect to FIGS. 1C, 1D and 6A-6F. Implant screw 102 is a threaded, substantially cylindrical object, with a frustoconical end 114 where its cylindrical cross-section tapers off. Extraction tool 104 can also be substantially cylindrical and hollow, such that when the system 100 is nested, extraction tool 104 surrounds at least a portion of rod 106 and interlocks with implant screw 102. Rod 106 passes through both extraction tool 104 and implant screw 102, such that a tip portion 132 of rod 106 extends past the frustoconical end 114 of implant screw 102, in the embodiment shown in FIG. 1A.

Implant screw 102 can be plasma coated in some embodiments. For example, implant screw 102 can be plasma coated with titanium to provide a textured surface. The plasma coating of implant screw 102 can provide a rough surface such that as bone grows around implant screw 102, the implant screw 102 is captured by interference fit with the regrown bone. Furthermore, the threads shown on implant screw 102 need not be driving threads. Rather, the threads of implant screw 102 as shown are more elongated. In one embodiment, for example, sacral thread 116 and ilial threads 122 extend further axially (i.e., from ilial portion 110 towards sacral portion 108) than radially (i.e., around the exterior of implant screw 102 perpendicular to the axial direction). Thus, rather than primarily serving to drive the screw, these threads facilitate fixation of implant screw 102 in the bone, and minimize breakage and/or cracking of the bone(s) during implantation. In some embodiments, plasma coating can be applied only to the smooth outer portions of screw 102, and not on the threaded portions 116, 122.

Rod 106 and/or extraction tool 104 can be used to drive implant screw 102 to a desired position, such as holding two bones in a desired spatial arrangement from one another. When implant screw 102 is in the desired position, extraction tool 104 and rod 106 can be removed. Notably, implant screw 102 does not include a pointed tip. Rather, as shown in FIGS. 1A-1B, rod 106 includes a pointed tip 132 that can be positioned to extend from a frustoconical end 114 of implant screw 102. Thus, rod 106 can be used to drive implant screw 102 into place and then be removed, leaving no sharp, pointed features embedded in the fused bone. Implant screw 102 then acts as a blind set screw, without a pointed tip or protruding head.

FIG. 1D shows a cross-section of the screw installation system 100 along line 1D-1D of FIG. 1C. As shown in FIGS. 1C and 1D, implant screw 102 includes sacral portion 108 and ilial portion 110, and defines apertures 112; extraction tool 104 includes screw engagement portion 126 and driver engagement portion 128; and rod 106 includes tip 132 and rod driver engagement portion 134, the features of which are shown in more detail in FIGS. 1C and 1D than in previous figures.

Implant screw 102 is designed to set a sacrum and an ilium, for example, in a fixed arrangement. As such, a sacral portion 108 is configured to be set in a sacrum, and an ilial portion 110 is configured to be set in an ilium. In the embodiment shown, sacral portion 108 includes a single screw thread 116, whereas ilial portion 110 includes multiple screw threads 122. Single screw thread 116 can help drive the screw 102 into the surrounding bone during insertion while maintaining high friction of insertion. Single screw thread 116 can also help with stability of the insert screw 102, and cause insert screw 102 to act substantially similarly to a lag screw having more threads on one end and relatively few or no threads on the other end.

Implant screw 102 defines apertures 112, which protrude through the cylindrical structure of implant screw 102 radially. Apertures 112 can be used to provide egress for materials such as bone growth promoters. As shown in FIG. 1C, implant screw 102 is generally hollow. As such, once positioned to affix an ilium and a sacrum, such bone growth material can be extruded from implant screw 102 through apertures 112. In some embodiments, bone growth material can further be extruded through the frustoconical front end 114 of the implant screw 102 (i.e., the distal end of sacral portion 108 through which tip 132 is arranged in the configurations shown with respect to FIGS. 1A-1D) once rod 106 is removed.

Extraction tool 104 includes screw engagement portion 126 and driver engagement portion 128. Extraction tool 104 can be used to drive implant screw 102 rotationally, in either clockwise or anticlockwise directions. By rotating implant screw 102 in this way, implant screw 102 can be backed out or removed from a bone in which it is positioned. Screw engagement portion 126, in the embodiment shown in FIGS. 1A-1D, has a hexagonal portion that engages with the inner radial diameter of ilial portion 110 of implant screw 102. Thus, rotation of extraction tool 104 causes co-rotation of implant screw 102. Driver engagement portion 128 is also a hexagonal portion, which can be mechanically coupled to a driver (not shown). Extraction tool 104 and implant screw 102 can be decoupled by laterally withdrawing extraction tool 104 from implant screw 102. In alternative embodiments, screw engagement portion 126 and driver engagement portion 128 need not be hexagonal, but could be any shape of spline configured to cause co-rotation with implant screw 102 and a driver, respectively, such as double or triple square, Bristol, or clutch screw drive systems, among others.

Rod 106 is configured to pass through implant screw 102 and extraction tool 104 in the nested arrangement. Rod 106 includes tip 132, which extends from the frustoconical end 114 of sacral portion 108, and rod driver engagement portion 134 at the opposite end of rod 106 from tip 132. Tip 132 is threaded in the embodiment shown in FIGS. 1A-1D, but in other embodiments could be, for example, an abrasive conical section or a helical pattern such as that found on a drill bit or auger bit. Driver engagement portion 134 of the rod 106 is configured to mechanically engage with another driver (not shown). In alternative embodiments the threading on insert screw 102 can be reversed such that rotating rod 106 counterclockwise drives screw 102 forwards, and rotating extraction tool 104 clockwise backs the insert screw 102.

By rotating rod 106, tip 132 can be used to sink insert screw 102 into bone. Often, as described with respect to FIGS. 6A-6F, a pilot hole or a threaded hole exists into which insert screw 102 is inserted. Rod 106 can be used to drive insert screw 102 further into the bone(s), while extraction tool 104 can be used to back insert screw 102 out of the bone(s). Once insert screw 102 is at a desired position, extraction tool 104 and rod 106 can be removed by pulling them axially away from insert screw 102.

FIGS. 2A-2D illustrate a system 200 that operates in a substantially similar fashion to the system 100 previously described with respect to FIGS. 1A-1D. Like system 100 of the previously-described Figures, system 200 includes screw 202, extraction tool 204, and rod 206, which perform similar functions to their counterparts in system 100 (reference numerals have been iterated by 100 to indicate like parts). Implant screw 202 includes sacral portion 208 and ilial portion 210, and defines apertures 212. Sacral portion 208 includes frustoconical end 214, sacral thread 216, and stop ledge 218. Ilial portion 210 includes engagement portion 220, ilial threads 222, and screw flange 224. Extraction tool 204 includes screw engagement portion 226, driver engagement portion 228, and body portion 230 there between. Rod 206 includes tip 232, rod driver engagement portion 234, shaft 236, and rod flange 238.

In contrast to the system 100 of FIGS. 1A-1D, system 200 of FIGS. 2A-2D has denser threading 222 at sacral portion 208 than at ilial portion 210, which contains a single thread 216. This can enable system 200 to function in a similar fashion to a lag screw, in that the threads 222 and the flange 224 can cooperate to draw together two materials (e.g. sacrum and ilium) in which the screw 202 is embedded.

Likewise, FIGS. 3A-3D illustrate a third embodiment of a system 300 that operates in a substantially similar fashion to the systems 100 and 200 previously described with respect to FIGS. 1A-1D and 2A-2D, respectively. System 300 includes implant screw 302, extraction tool 304, and rod 306. Implant screw 302 includes sacral portion 308 and ilial portion 310, and defines apertures 312. Sacral portion 308 includes frustoconical end 314, sacral thread 316, and stop ledge 318. Ilial portion 310 includes engagement portion 320, ilial threads 322, and screw flange 324. Extraction tool 304 includes screw engagement portion 326, driver engagement portion 328, and body portion 330 there between. Rod 306 includes tip 332, rod driver engagement portion 334, shaft 336, and rod flange 338.

In contrast to the earlier-described systems 100 and 200, the density of threading 322 is relatively higher, with a much narrower pitch. This change in pitch of threading 322 can be helpful for driving insert screw 302 into relatively stronger materials, at a lower rate of forward movement per rotation.

Likewise, FIGS. 4A-4D illustrate a fourth embodiment of a system 400 that operates in a substantially similar fashion to the systems 100, 200, and 300, previously described with respect to FIGS. 1A-1D, 2A-2D, and 3A-3D, respectively. System 400 includes implant screw 402, extraction tool 404, and rod 406. Implant screw 402 includes sacral portion 408 and ilial portion 410, and defines apertures 412. Sacral portion 408 includes frustoconical end 414, sacral thread 416, and stop ledge 418. Ilial portion 410 includes engagement portion 420, ilial threads 422, and screw flange 424. Extraction tool 404 includes screw engagement portion 426, driver engagement portion 428, and body portion 430 there between. Rod 406 includes tip 432, rod driver engagement portion 434, shaft 436, and rod flange 438.

In this embodiment, the densely threaded portion 422 is disposed on the sacral portion 408, and the single thread 416 is disposed on the ilial portion 410. As such, the screw 402, when inserted in two materials such as a sacrum and an ilium, can act as a lag nut to bring together those materials. The flange 428 can hold one of the bones while the threads 422 apply a force on the second bone towards the first bone.

In alternative embodiments, various other threading pitches and thread sizes (e.g., extent of radial protrusion from the other radial wall of the insert screw) can be used. For example, in embodiments, the thread size can be between 1.0 and 1.5 mm, for an insert screw having an 8.0 mm diameter. In embodiments, the diameter of the flange (e.g., flange 124) can be the same as the diameter of the insert screw plus the thread size.

Figure 5B:
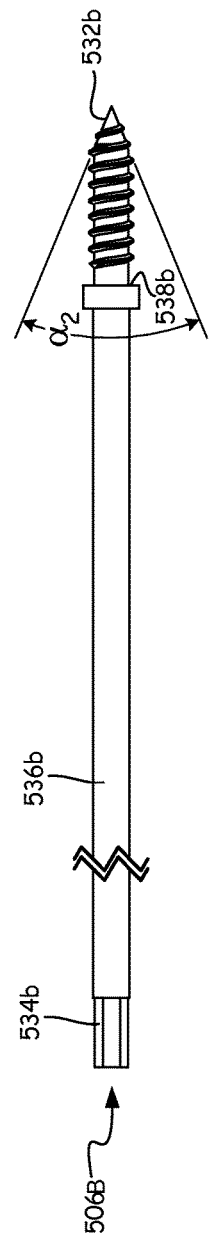
Figure 5C:
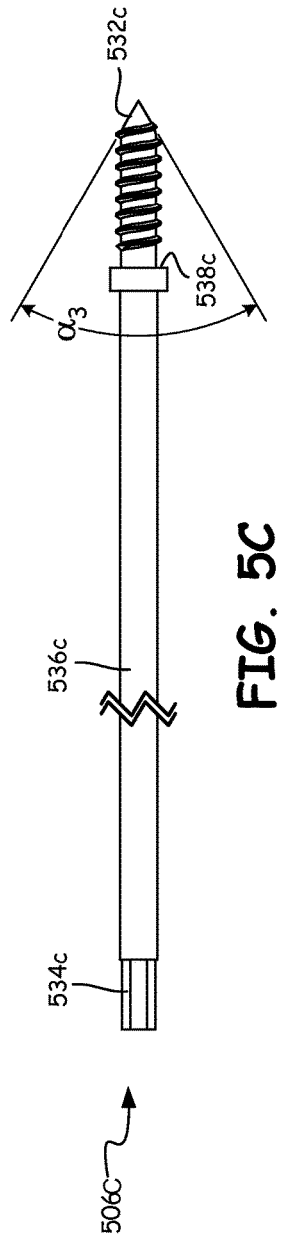

FIGS. 5A-5C are elevation views of three rods 506A-506C, respectively, illustrating various angles of attack $\alpha 1$, $\alpha 3$, and $\alpha 3$. The rods 506A-406C shown in FIGS. 5A-5C are similar in function to rods 106, 206, 306, and 406 as described with respect to the previous figures. In FIGS. 5A-5C, and throughout the application generally, reference numerals are iterated by factors of 100 to identify those parts that are similar in form and/or function to previously described features.

In various embodiments, angle of attack $\alpha$ can be relatively more steep or narrow to produce a variety of benefits. For example, angle of attack $\alpha 1$, shown in FIG. 5A, is about 30°, angle of attack $\alpha 2$, as shown in FIG. 5B, is about 45°, and angle of attack $\alpha 3$, as shown in FIG. 5C, is about 60°. Modifying angle of attack $\alpha$, or the spacing of threads on tip (532a-532c), can change the lead of the tip 532. Angle of attack $\alpha$ can be modified to correspond to an angle present on a corresponding implant screw (e.g., implant screws 102, 202, 302, and 402 of the previously-described embodiments). The lead tip can be helpful in finding the drilled hole in the bone (as described in more detail with respect to FIGS. 15A-15F) that was made through the muscle. The tip 532 can facilitate finding the screw hole without use of a guide wire, for example. Depending on the age and bone density of the patient, the force required to drive an accompanying screw can vary. Modification off angle of attack $\alpha$ can compensate for these factors.

FIGS. 5A-5C also show rod flanges 538a-538c, respectively, arranged a length L from the tip (532a-532c). Rod flanges 538a-538c are arranged between the tip 532a-532c and rod driver engagement portion 534a-534c, respectively, in each figure. As shown in FIGS. 5A-5C, rods 506A-506C are substantially cylindrical, and the rod flange (538a-538c) of each rod extends radially outward from cylinder defined by the shaft (536a-536c) of each rod 506A-506C. Each rod flange (538-538c) can engage with a portion of an insert screw such that axial thrust is transferred from that rod (506A-506C) to the insert screw 506a-506c.

FIGS. 6A-6F are various views of insert screw 602, according to an embodiment. Insert screw 602, like its counterparts previously described with respect to other figures, is a substantially cylindrical, right-hand threaded screw having a sacral portion 608 and an ilial portion 610. Sacral portion 608 includes a single thread 616 whereas ilial portion 610 is more densely threaded with ilial threads 622. Sacral portion 608 terminates in a threaded interior portion 615, radially inwards of a frustoconical end section 614. Insert screw 602 is hollow to permit another component, such as a rod having a tip, to pass through the frustoconical section 614. Insert screw 602 defines apertures 612 through which material such as bone growth promoters can be routed. Additionally, bone can grow through the hollow portions of insert screw 602. Insert screw 602 can be made of a variety of materials, such as titanium or titanium alloys, and can be treated with a plasma coating or hydroxy-appetite to add desired surface finish and/or texture.

FIG. 6B is a cross-sectional view of insert screw 602, illustrating internal threaded portion 615 and stop ledge 618. Internal threaded portion 615 can engage with a corresponding threaded portion passing therein, such as the tip of a rod (e.g., tips 132, 232, 332, or 432 of previously-described embodiments). Stop ledge 618 also can interact with a component arranged within insert screw 602. For example, stop ledge 618 can be configured to interact with a flange (e.g., rod flanges 538a-538c) to transfer axial loads between insert screw 602 and a component passing through insert screw 602 such as a rod.

FIG. 6C illustrates a cross-section through line C-C of FIG. 6B. The cross-section shown passes through an aperture 612 defined by insert screw 602. Aperture 612 has a width w, which can vary in embodiments depending upon the amount, type, and viscosity of bone growth material or other material (such as coagulants or antibiotics) that is to be routed through aperture 612.

FIG. 6D is an end view of the insert screw 602 from the side of flange 624. On the radially inner edge of ilial portion 610 are engagement features 620. In the embodiment shown with respect to FIG. 6D, engagement features 620 comprise a hexagonal screw head, which can be engaged with a mating hexagonal structure in a corresponding extraction tool such as an extraction tool. As shown in FIG. 6D, the radial inner edge of ilial portion 610 distally of engagement features forms a circle. The radius of the radial inner edge of ilial portion 610 in the embodiment shown in FIG. 6D could be, for example, 5 mm. Furthermore, the radius of the radial outer edge of ilial portion 610 in the embodiment shown in FIG. 6D could be, for example, 10 mm. Threads 622 on the exterior of insert screw 602 add to this radial outer width in portions.

FIG. 6E depicts insert screw 602 having a frustoconical portion 614 that is inclined by an angle β with respect to the primary axis along which insert screw 302 extends. In various embodiments, β can be 30°, 45°, or 60°, for example. In some embodiments, β will be equal to the angle α corresponding to the level of incline of the rod tip configured to pass through insert screw 602, as previously described with respect to FIGS. 5A-5C. FIG. 6E further depicts an external flange 624 at the distal end of ilial portion 610. External flange 624 can prevent implant screw 602 from being driven too deeply into the bone, for example. Additionally, external flange 624 can cause implant screw 602 to function as a lag screw end and allow the two connected parts (e.g., ilium and sacrum) to be driven towards one another, as previously described with respect to FIGS. 4A-4D.

In one particular embodiment, insert screw 602 has a total length (i.e., from one end of sacral portion 608 to the distal opposite end of ilial portion 610) of 30 mm, a total radial width of 10 mm, and an internal radial width through ilial portion 610 of 5 mm. In that embodiment, sacral portion 608 (i.e., the portion radially outwards of internal threading 615) has a total axial length of 10 mm, ilial portion 610 (i.e., the portion having denser threading) has a total axial length of 7.50 mm, β is 46.40°, apertures 612 have a width w of 2 mm, and external flange 624 has an axial thickness of 1.08 mm. In some embodiments, hexagonal features of the engagement portion 620 have a minimum radial width of 5 mm and a maximum radial width of 5.77 mm.

FIGS. 7A-7E depict an insert screw 702 that is substantially similar in function to the insert screws previously described. Many aspects of insert screw 702, such as apertures 712, frustoconical portion 714, internal threading 715, single thread 716, stop ledge 718, engagement features 720, threads 722, and external flange 724 are substantially similar to their counterparts previously described with respect to FIGS. 6A-6E. In contrast to insert screw 602 previously described with reference to FIGS. 6-6E, insert screw 702 has relatively denser threading at sacral portion 708 than at ilial portion 710. Insert screw 702, therefore, provides the benefits previously described with respect to insert screw 402 shown in FIGS. 4A-4D.

Likewise, FIGS. 8A-8E depict an insert screw 802 that is substantially similar in function to the insert screws previously described. Many aspects of insert screw 802, such as apertures 812, frustoconical portion 814, internal threading 815, single thread 816, stop ledge 818, engagement features 820, threads 822, and external flange 824 are substantially similar to their counterparts previously described with respect to FIGS. 6A-6E. Insert screw 802 of FIGS. 8A-8E provides the benefits previously described with respect to insert screw 302 previously described with respect to FIGS. 3A-3D, and has denser threading at ilial portion 810 than at sacral portion 808.

Likewise, FIGS. 9A-9E depict an insert screw 902 that is substantially similar in function to the insert screws previously described. Many aspects of insert screw 902, such as sacral portion 908, ilial portion 910, apertures 912, frustoconical portion 914 having angle β, internal threading 915, single thread 916, stop ledge 918, engagement feature 920, threads 922, and external flange 924 are substantially similar to their counterparts previously described with respect to FIGS. 6A-6E. Insert screw 902 of FIGS. 9A-9E has a greater length than, for example, insert screw 702 of FIGS. 7A-7E. Because the densely spaced threads 922 of insert screw 902 are positioned opposite the flange 924, insert screw 902 can be used as a lag bolt, as described with respect to previously-shown figures.

FIGS. 10A-10D are elevation views of four embodiments of insert screws; 1002a, 1002b, 1002c, and 1002d, respectively. In various embodiments, the overall length $L_t$ of each insert screw can be modified to account for an expected distance between bones as well as the shape of the ilium and sacrum to be joined using the insert screw 1002a, 1002b, 1002c, or 1002d, or the extent to which the insert screw 1002a, 1002b, 1002c, or 1002d is to be embedded within those bones. In some embodiments, described herein with respect to FIG. 15F, for example, multiple insert screws can be used to affix bones together, and the lengths of the insert screws used to do so can vary, while in other embodiments they can be the same length.

Figure 10A:
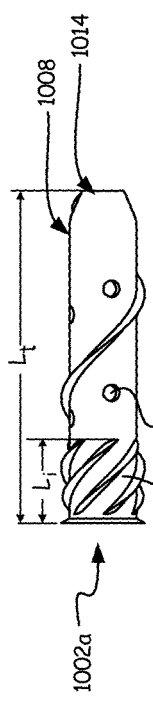
FIGS. 10A-10D are elevation views of implant screws having different lengths, according to a first thread arrangement.
Figure 10B:
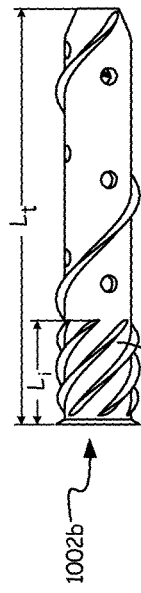
Figure 10C:
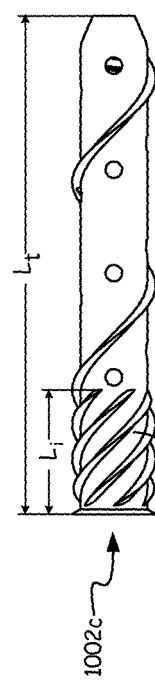
Figure 10D:
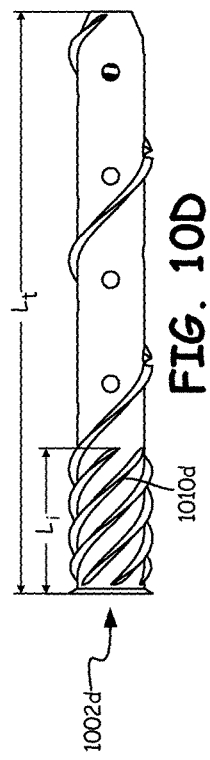
Figure 11A:
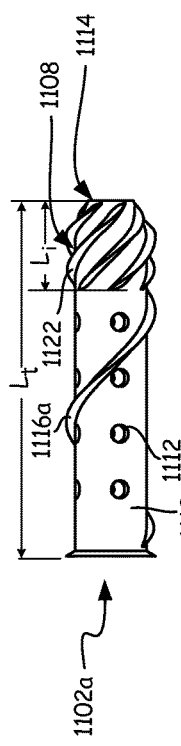
FIGS. 11A-11D are elevation views of implant screws having different lengths, according to a second thread arrangement.
Figure 11B:
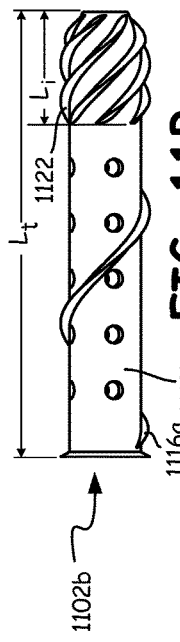
Figure 11C:
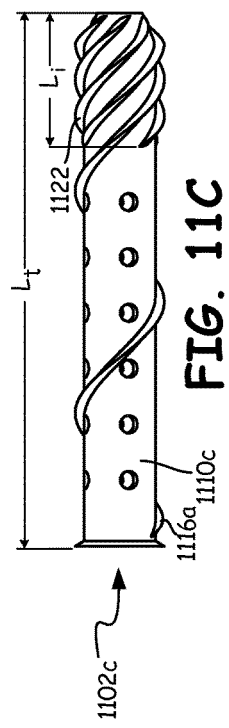
Figure 11D:
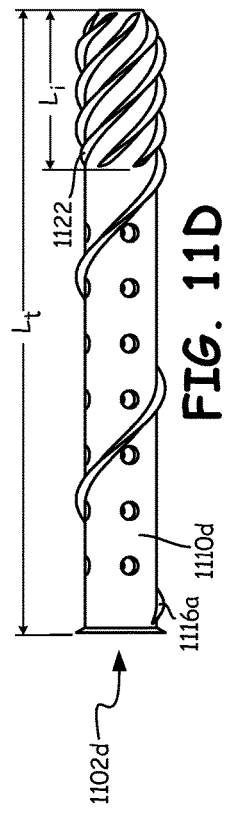
Figure 13A:
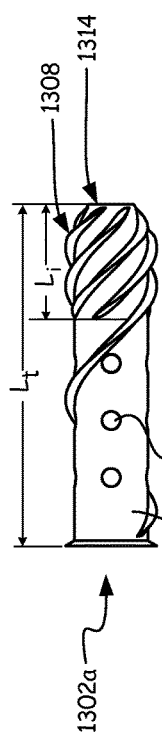
FIGS. 13A-13D are elevation views of implant screws having different lengths, according to a fourth thread arrangement.
Figure 13B:
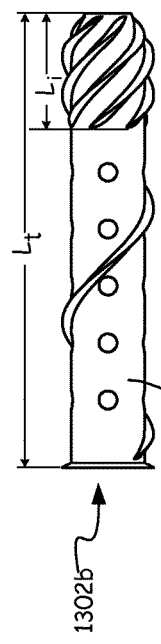
Figure 13C:
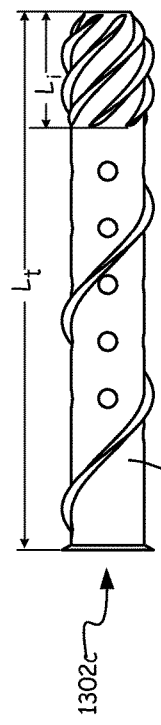
Figure 13D:
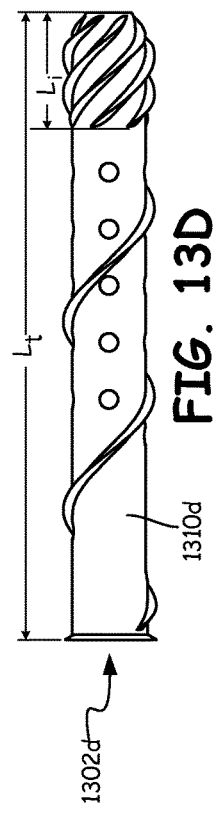

In the embodiment shown in FIG. 10A, insert screw 1002a includes sacral portion 1008 and frustoconical end 1014, opposite from iliac portion 1010a. Insert screw 1002a has a total length $L_t$ of 40 mm, while iliac portion 1010a has an iliac length $L_i$ of 10 mm. In the embodiment shown in FIG. 10B, insert screw 1002b has a total length $L_t$ of 50 mm, while iliac portion 1010b has an iliac length $L_i$ of 12 mm. In the embodiment shown in FIG. 10C, insert screw 1002c has a total length $L_t$ of 60 mm, while iliac portion 1010c has an iliac length $L_i$ of 15 mm. In the embodiment shown in FIG. 10D, insert screw 1002d has a total length $L_t$ of 70 mm, while iliac portion 1010d has an iliac length $L_i$ of 17 mm. In each of the embodiments of insert screw 1002a-1002d shown with respect to FIGS. 10A-10D, the internal and external radii could be, for example, 8 mm and 10 mm, respectively, as previously described with respect to FIG. 6D. With increasing total length $L_t$, additional apertures 1012 can be defined by insert screw 1002a, 1002b, 1002c, or 1002d.

FIGS. 11A-11D depict four embodiments of insert screws 1102a, 1102b, 1102c, and 1102d. In the embodiment shown in FIG. 11A, insert screw 1102a includes sacral portion 1108 and frustoconical end 1114, thread 1116a, denser threading 1122, and iliac portion 1110a. Apertures 1112 are positioned along the length $L_t$ of insert screw 1102a except for the sacral portion 1108, shown as having length $L_i$. The more densely threaded sacral portion 1108 in each of the Figures facilitates the use of the respective insert screw as a lag screw with iliac portions 1110a-1110d as the shaft portion (since they are substantially smooth other than thread 1116a-1116d), as previously described.

FIGS. 12A-12D depict four additional embodiments of insert screws 1202a, 1202b, 1202c, and 1202d. In the embodiments shown, sacral portion 1208 and frustoconical end 1214 are arranged opposite from the respective iliac portion (1210a-1210d). Apertures 1212 and a single thread (1216a-1216d) are arranged along the length $L_t$ of the screws (1202a-1202d), except for the iliac length $L_i$. In the embodiments shown in FIGS. 12A-12D, the pitch of the more densely spaced threads 1222a, 1222b, 1222c, and 1222d is reduced, as compared to previously described embodiments.

FIGS. 13A-13D depict four additional embodiments of insert screws 1302a, 1302b, 1302c, and 1302d. The embodiments shown illustrate sacral portion 1308 (having length $L_i$) and frustoconical portion 1314 opposite from iliac portion 1310a-1310d. Apertures 1312 are positioned along a portion of the length $L_t$ of the screw 1302a-1302d. The insert screws 1302a, 1302b, 1302c, and 1302d are of different lengths from one another, and show that the portion of each screw covered by dense threading 1322a-1322d can vary, for example, as compared to the embodiments shown in FIGS. 11A-11D.

FIGS. 14A-14D show an embodiment of an extraction tool 104, previously described with respect to FIGS. 1A-1D. Extraction tool 104 can be used to rotate an insert screw (e.g., insert screw 102 of FIGS. 1A-1D) to change its position or remove it from a material in which it is embedded. In the embodiment shown in FIGS. 14A-14D, extraction tool 104 includes a hexagonally patterned section at each of screw engagement portion 126 and driver engagement portion 128. In another configuration, the extraction tool can have an octagonal, or pentagonal section to engage the corresponding section at each end of the screw portion 126. Likewise the back end of the screw, 310, would have the same shape to correspond with the extraction tool.

These portions 126 and 128 facilitate splining of extraction tool 104 to adjacent components. For example, screw engagement portion 104 can be mechanically coupled to an insert screw (not shown) having portions, such as engagement features, that are shaped to mate with the screw engagement portion 126. Likewise, driver engagement portion 128 is configured to engage with a driver (not shown), which could be hand-operated or mechanically powered, such as a chuck on a drill. In this way, torque can be applied on the insert screw remotely, via the extraction tool 104.

The length of extraction tool 104 can vary depending on a length that the tool can need to travel from the operator/driver (not shown) to engage with a screw. The length of the screw engagement portion $L_{126}$ can also vary. In the embodiment shown with respect to FIGS. 14A-14D, engagement portion length $L_{126}$ is 8 mm. Likewise, the length of driver engagement portion 128 can be equal to, longer than, or shorter than engagement portion length $L_{126}$, and in various embodiments it need not have the same geometric shape. For example, screw engagement portion 126 could be hexagonal whereas driver engagement portion 128 could be octagonal, square, or any other pattern configured to engage with another component for the transmission of radial force, and vice versa.

FIG. 14C is a cross-sectional view of extraction tool 104 taken from line 14C-14C of FIG. 14B. FIG. 14C illustrates width $W_{104}$ of the radial inner passage through extraction tool 104. In the embodiment shown in FIG. 14C, width $W_{104}$ is about 3.5 mm. Typically, the width $W_{104}$ of the radial inner passage of a given extraction tool (e.g., extraction tool 104) is larger than the radial width of a corresponding rod (e.g., rod 106 of FIGS. 1A-1D), such that the rod can pass through extraction tool 104.

FIG. 14D is an end view of extraction tool 104 taken from an end view of FIG. 5C. As previously described with respect to the insert screw 602 of FIG. 6D, extraction tool 104 includes splining features that can, in some embodiments, have a width of 5 mm. The inner radius r1 of the inner passage could be, for example, about 1.75 mm, and the outer radius r2 of body portion 130 could be about 2.9 mm, in some embodiments. Extraction tool 104 comprises a solid, male connector (screw engagement portion 126) that couples with a female connector cavity (engagement portion 120) of insert screw 102.

FIGS. 15A-15F show a variety of steps that can be used to perform implantation of a screw to fuse an ilium 1550 to a sacrum 1552. In some embodiments, a patient is positioned prone on bolsters to raise the hips in addition to rolls or padding under the chest. The Posterior Superior Iliac Spine (PSIS) 1554 can then be identified and/or marked. A lateral fluoroscopy view can be obtained to identify the posterior sacral laminar line 1558 and the Alar line 1560. An incision can be made 2-6 cm lateral to the PSIS, depending on the size of the patient. A guide pin 1556 can then be placed, under lateral fluoroscopy x-ray, within the acute angle formed by the sacral laminar line 1558 and the Alar line 1560. The trajectory of the guide pin is such that it will engage the ala and sacrum, pointing downward toward the apex of the sacral-alar angle. The Guide pin 1556 can be tamped with a mallet until it passes the sacroiliac joint, avoiding the sacral foramina under the outlet X-ray view. Inlet and Lateral views are also checked to avoid ventral violation of the sacrum. This is shown, for example, in FIG. 15A.

Figure 15A:
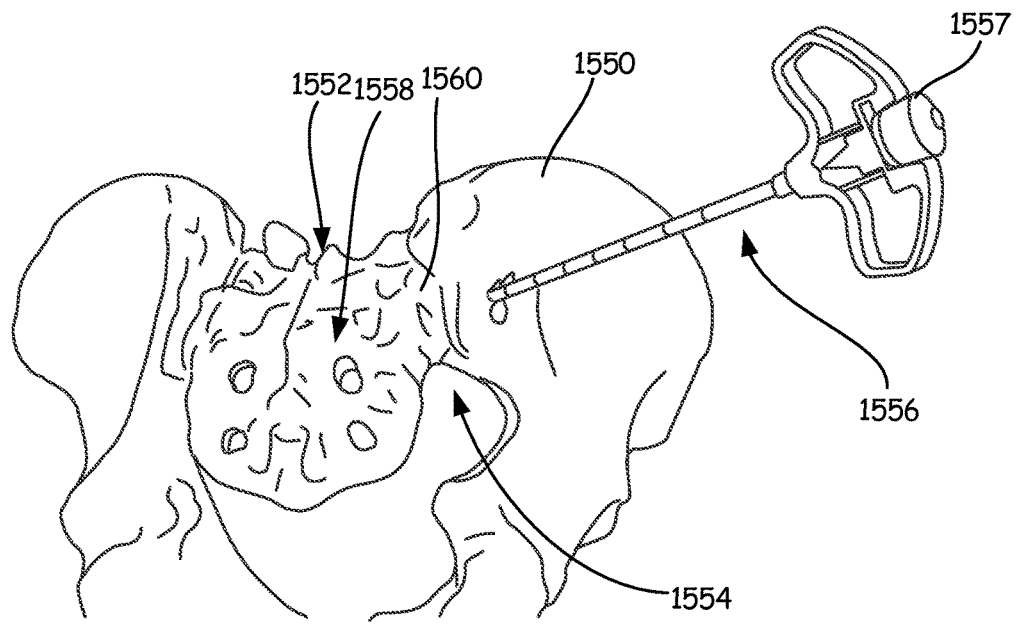
FIGS. 15A-15J depict various stages of insertion of an insert screw, including interaction between an awl tool, an awl tool with the stylette removed, a drill, various insert screws, and an ilium and sacrum, according to an embodiment.
Figure 15B:
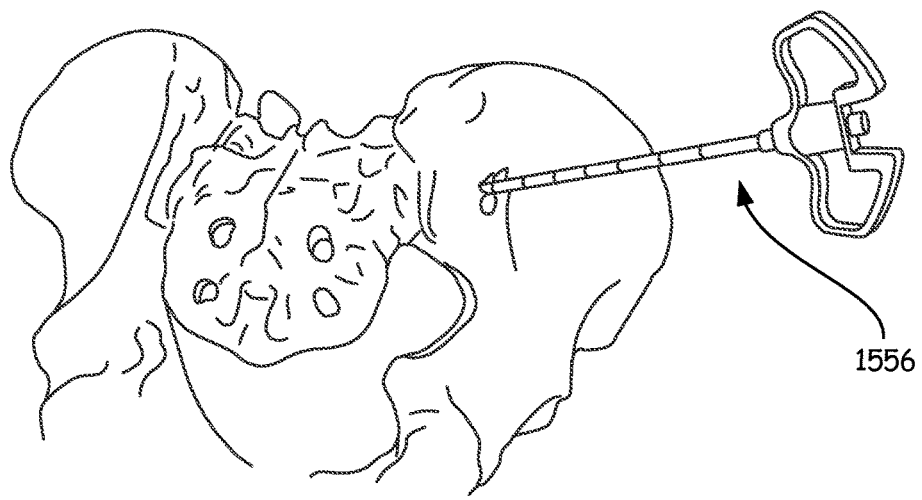
Figure 15C:
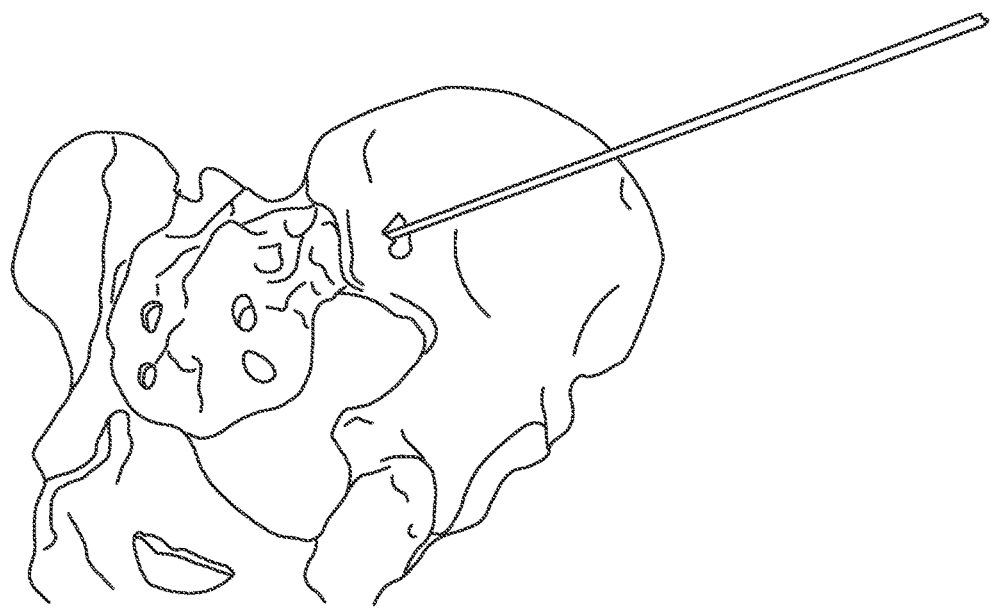
Figure 15D:
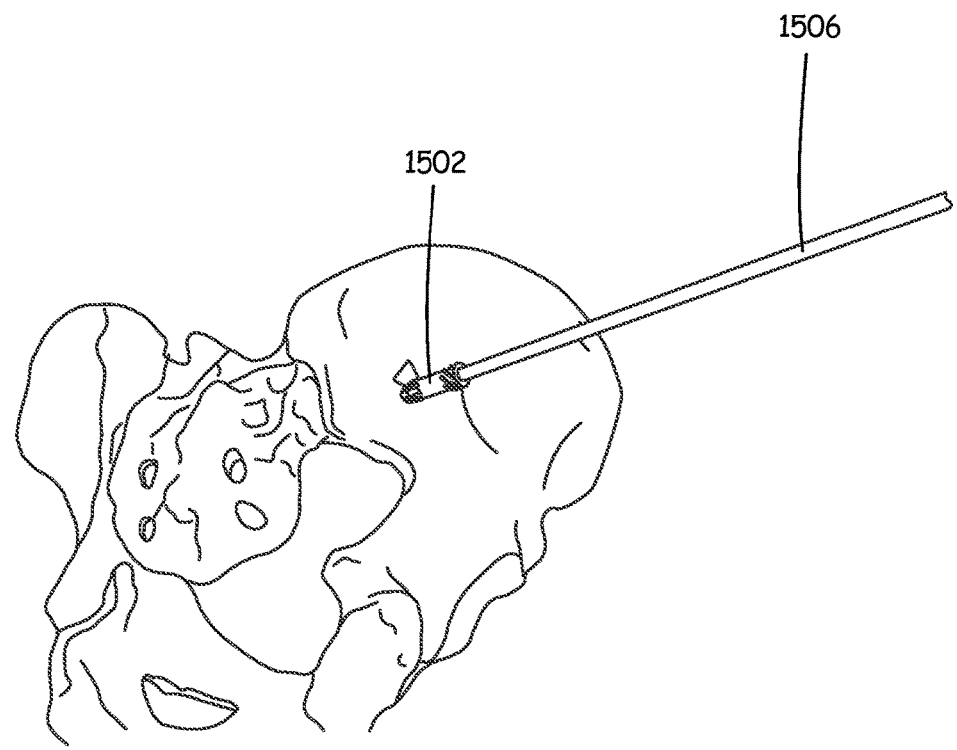
Figure 15E:
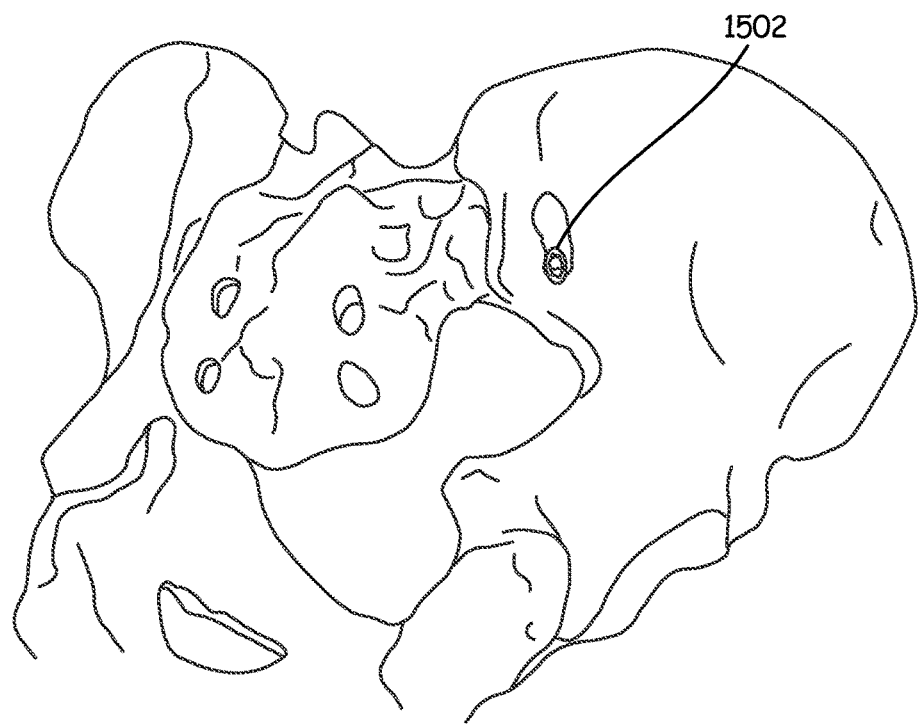

As shown in FIG. 15B, the guide pin handle 1557 is removed. A muscle protector sleeve (not pictured) can be attached to the Tap. The Tap/muscle protector is placed over the pin. The Tap is marked to allow sizing of the implant. The Tap is inserted pass the SI joint. The guide pin, and tap/muscle protector are removed. The correct size of implant screw 1502 can be assembled with the threaded rod 1506, as shown in FIG. 15D. A muscle protector sleeve can be assembled over the implant/rod. The handle can be attached to the threaded rod. The implant/threaded rod can be inserted into the tapped hole. The implant can be driven past the sacro-iliac joint by turning the handle clockwise in the embodiment shown with respect to FIG. 15D, although in alternative embodiments the screw could be left-hand threaded. When approaching the sacral foramina under the outlet-x-ray view, the handle from the rod can be removed. The extraction tool (e.g., extraction tool 104 as shown in FIGS. 1A and 1B) can be placed over the rod 1506 to engage the back end of the implant. The extraction tool facilitates minor adjustments either clockwise or counter-clockwise.

In some embodiments, demineralized bone matrix (DBM) or other bone growth material can be injected into the back open end of the extraction tool with a syringe; the hollow chamber of the extraction tool can function as a funnel. An inner stylet can then be placed into the back end of the extraction tool to push the DBM through the screw. The extraction tool can be removed including any excess DBM.

Figure 15F:
Figure 15G:
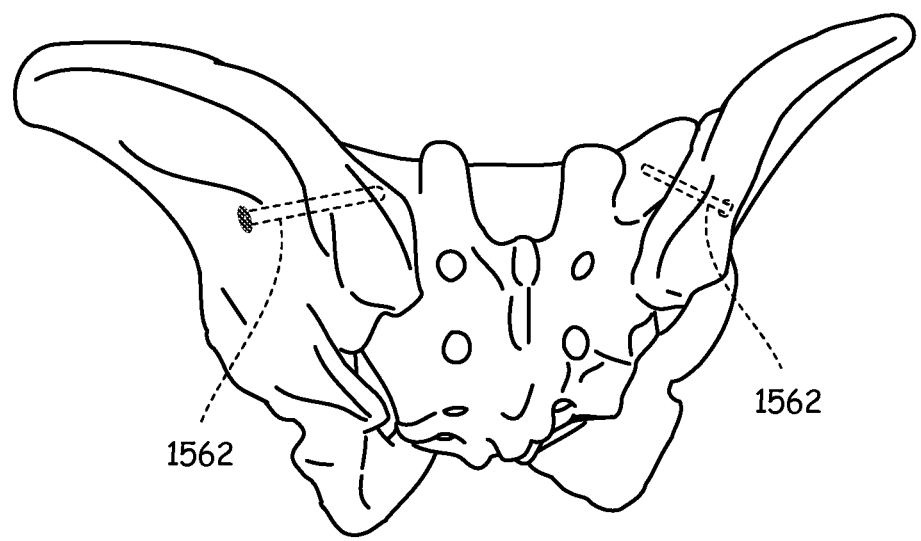
Figure 15H:
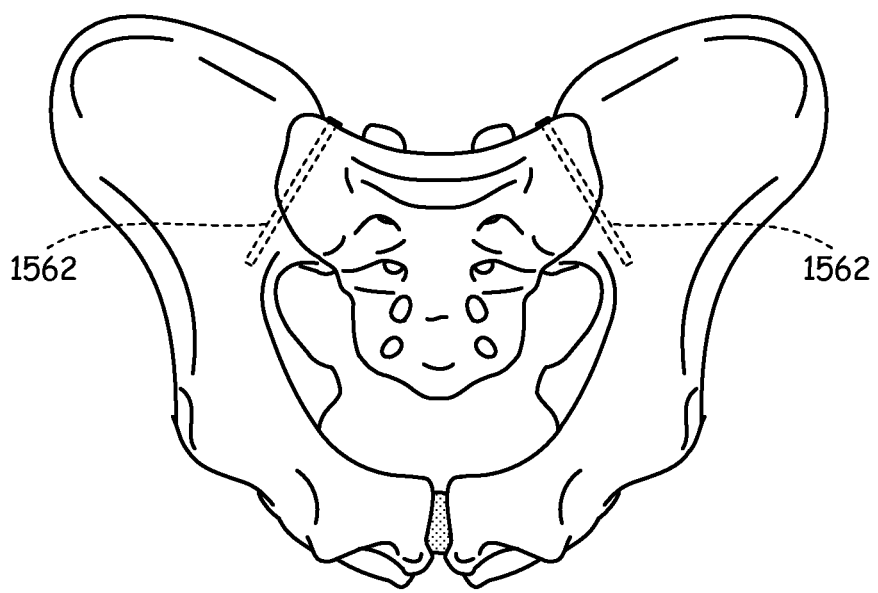
Figure 15I:
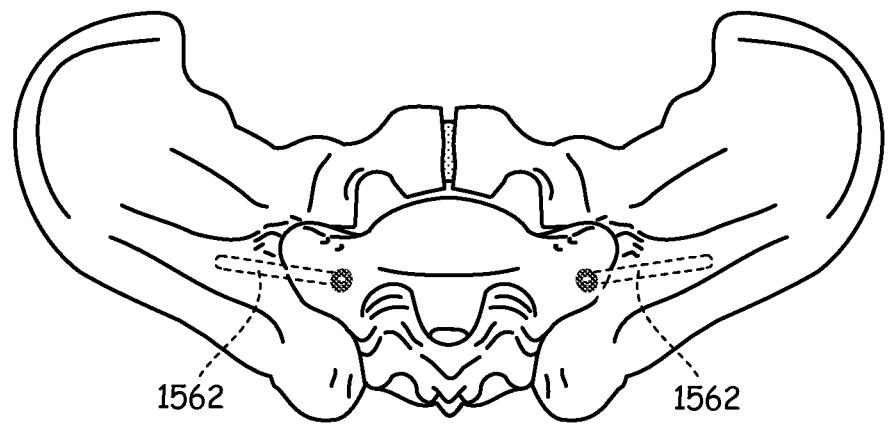
Figure 15J:
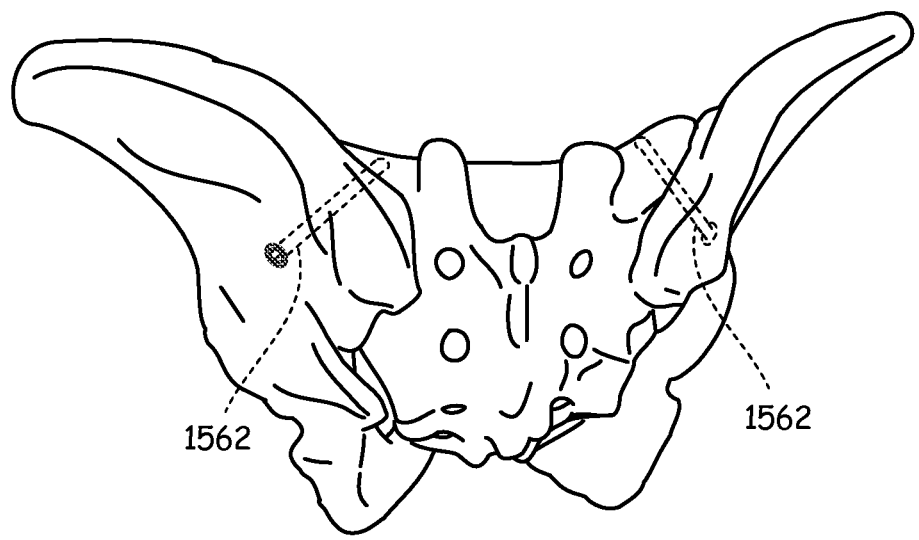

As shown in FIG. 15F, additional implant screws can be added as necessary to fuse the sacro-iliac joint. These screws can have different lengths, widths, and other features as previously described with respect to earlier figures. Embodiments as shown herein can be used to accurately and efficiently place implant screws within bones to fuse them, without leaving sharp tips that can cause discomfort and/or injury. Furthermore, the open-tipped design of the implant screws shown herein, as well as apertures defined in their sides, can be used to apply bone growth material or other substances to the affected bones. The hollow interior of the screw also helps promote bone growth and fusion.

FIG. 15G-15J illustrate a sacrum and ilium, and further illustrate the location of insertion sites 1562. Insertion sites 1562 are potential locations for positioning insert screws such as those previously described in order to fuse the sacrum with the ilium.

Figure 16A:
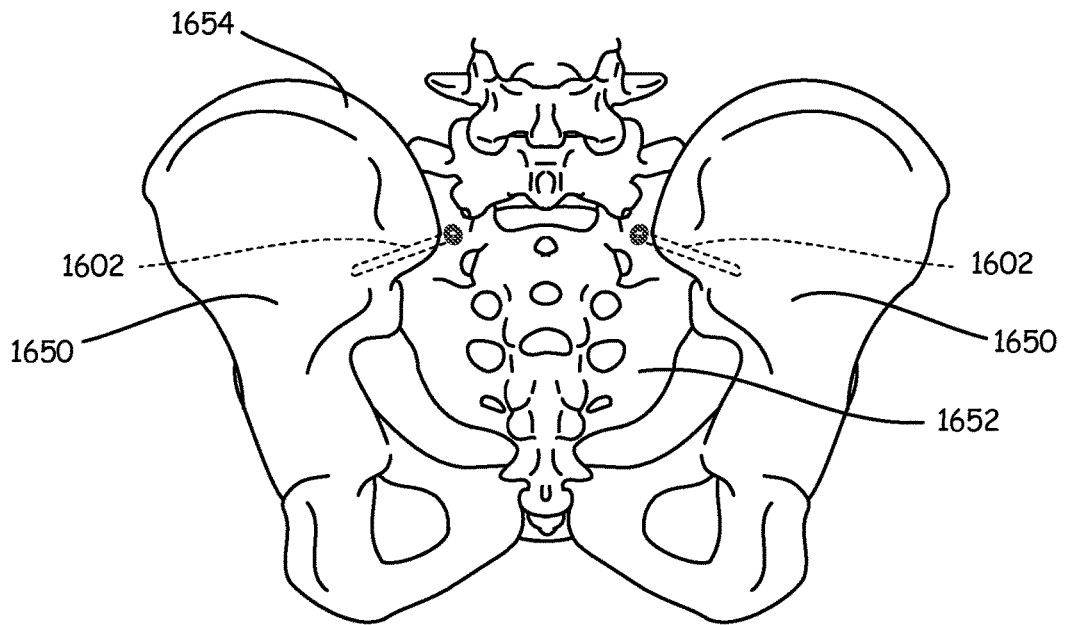
FIGS. 16A-16D depict an alternative insertion scheme for a sacro-iliac screw.
Figure 16B:
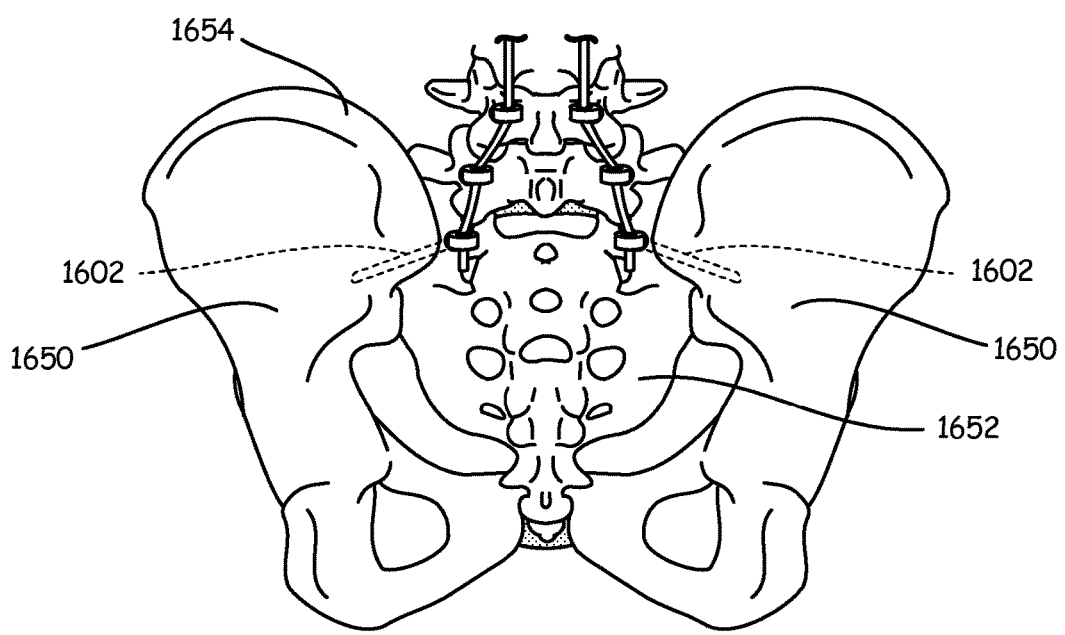
Figure 16C:
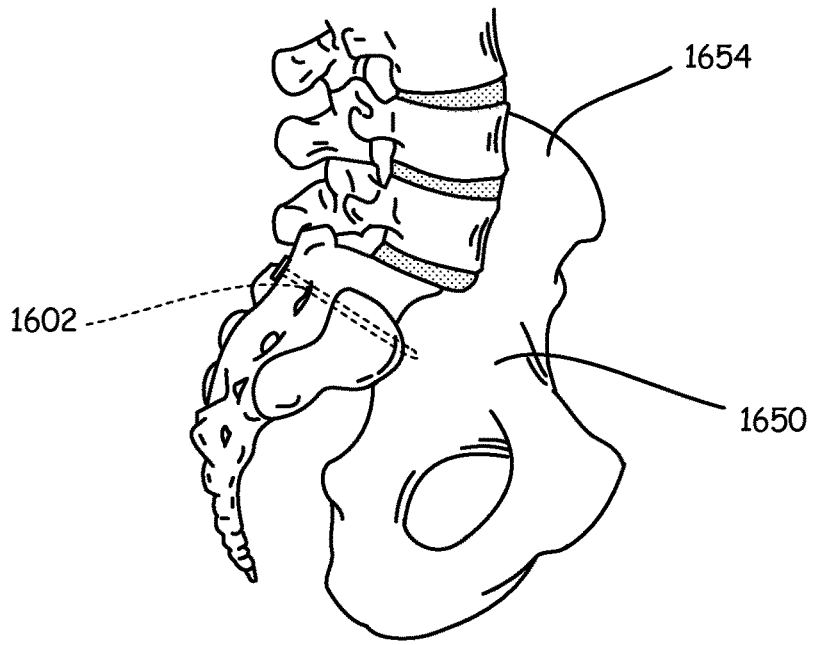
Figure 16D:
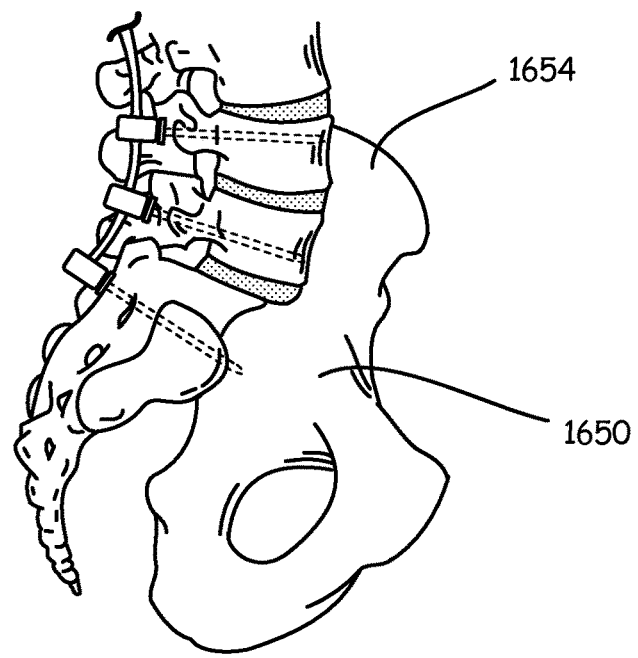

FIGS. 16A-16D illustrate an alternative placement of insert screws that can be used to fuse the sacrum and ilium. FIGS. 16A-16D show insert screw 1602, ilium 1650, sacrum 1652, and PSIS 1654. As illustrated in the embodiment of FIGS. 16A-16D, the insert screws can be inserted through a midline or lateral incision at the L5-S1 via a minimally invasive approach. The insert screw or screws could also be inserted through an open approach. In this embodiment, the insert screw goes from the sacrum to the ilium, rather than from the ilium to the sacrum as previously described. According to one embodiment, the screw can have a head to attach to another implanted component, as shown in FIG. 16D. If the previously-described insert screws are used according to this procedure, then the sacral portion and the ilial portion would be reversed, as the direction of insertion is opposite from that previously described.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

The invention claimed is:

1. An implant screw adapted for implantation into one or more bones of a patient, comprising:
    a proximal portion having an open proximal end, a generally cylindrical outer surface and an inner surface defining a generally hollow interior, the inner surface further defining engagement features adapted to be engaged to enact rotation of the implant screw, the proximal portion further including an external flange at the open proximal end configured to interface with a bone of the patient to prevent further rotation of the implant screw from advancing the implant screw further into the bone; and
    a distal portion unitarily formed with the proximal portion as a single unitary part, the distal portion having a body portion with a generally cylindrical outer surface and a frustoconical distal end portion defining an open distal tip, the distal portion further including a threaded inner surface defining a generally hollow interior, the inner surface further defining an inwardly projecting stop ledge such that the generally hollow interior of the distal portion is narrower than the generally hollow interior of the proximal portion,
    wherein the stop ledge is configured to engage with a corresponding feature on a rod configured to rotate the implant screw and the frustoconical portion is configured to provide egress from the implant screw of a tip of the rod, and
    wherein the threaded inner surface of the distal portion is provided on a distal-most portion of the generally hollow interior of the distal portion.

2. The implant screw of claim 1, wherein:
    the outer surface of the proximal portion comprises one or more first threads; and the outer surface of the distal portion comprises one or more second threads, the first threads and second threads being elongated along a long axis of the implant screw.

3. The implant screw of claim 1, wherein the engagement feature is configured to mate with an extraction tool.

4. The implant screw of claim 1, wherein the implant screw is at least partially plasma coated.

5. The implant screw of claim 4, wherein the plasma coating comprises titanium.

6. The implant screw of claim 1, further comprising a plurality of apertures extending between the outer surfaces and the inner surfaces of both the proximal portion and the distal portion.

7. The implant screw of claim 1, wherein all of the generally hollow interior of the distal portion is threaded.

8. The implant screw of claim 1, wherein threading configured to facilitate driving the implant screw into the bone is disposed only on the proximal portion and not on the distal portion.

* * * * *